(12) United States Patent
Webb

(10) Patent No.: US 11,931,070 B1
(45) Date of Patent: Mar. 19, 2024

(54) HALF PIPE CANNULA AND METHODS OF MANUFACTURING AND USING HALF PIPE CANNULA

(71) Applicant: Hybrid Cannula LP, Allen, TX (US)

(72) Inventor: Jonathan H. Webb, Allen, TX (US)

(73) Assignee: HYBRID CANNULA LP, Allen, TX (US)

(*) Notice: Subject to any disclaimer, the term of this patent is extended or adjusted under 35 U.S.C. 154(b) by 128 days.

(21) Appl. No.: 17/163,140

(22) Filed: Jan. 29, 2021

Related U.S. Application Data

(60) Provisional application No. 62/967,960, filed on Jan. 30, 2020.

(51) Int. Cl.
*A61B 17/34* (2006.01)
*A61M 25/00* (2006.01)

(52) U.S. Cl.
CPC ...... *A61B 17/3431* (2013.01); *A61B 17/3423* (2013.01); *A61M 2025/006* (2013.01)

(58) Field of Classification Search
CPC ............ A61B 17/0482; A61B 17/0057; A61B 17/0218; A61B 17/3421; A61B 17/3423; A61B 17/3431; A61B 17/3468; A61B 17/3462; A61B 2017/3425; A61B 2017/3441; A61B 2017/3445; A61B 2017/3433; A61B 2017/348;
(Continued)

(56) References Cited

U.S. PATENT DOCUMENTS 5,320,611 A  6/1994  Bonutti et al.
5,573,517 A  11/1996 Bonutti et al.
(Continued)

FOREIGN PATENT DOCUMENTS

EP  1908428 A1  4/2008
EP  1908428 B1  1/2011
(Continued)

OTHER PUBLICATIONS

Dry-Doc Cannula Leak Prevention System product sheet and web site product information, ConMed Linvatec, Largo, FL, Sep. 2008, CBR 3035 Rev. 1, 3 pages.
(Continued)

*Primary Examiner* — Brooke Labranche
*Assistant Examiner* — Lindsey R. Rivers
(74) *Attorney, Agent, or Firm* — SPRINKLE IP LAW GROUP

(57) ABSTRACT

A half pipe cannula has a first portion and a second portion. The first portion, which includes a proximal end and an elongated tab along the length of the first portion, can be formed from a first material with a selected rigidity. The second portion, which includes a proximal end, a cannulated passage, and a distal end, can be formed from a second material with a selected flexibility. The second portion of the half pipe cannula partially or fully overlaps the elongated tab of the first portion of the half pipe cannula. The second portion of the half pipe cannula has surface features such as a thread or bumper feature. Each portion of the half pipe cannula may have one or more flanges on either end or both ends. The second portion of the half pipe cannula can be made of a flexible material such as thermoplastic elastomer.

21 Claims, 19 Drawing Sheets

(58) Field of Classification Search
CPC .... A61B 2017/3482; A61B 2017/3484; A61B 2017/3447; A61M 29/00
See application file for complete search history.

(56) References Cited

U.S. PATENT DOCUMENTS

| | | | |
|---|---|---|---|
| 5,601,590 A | 2/1997 | Bonutti et al. | |
| 5,667,500 A | 9/1997 | Palmer et al. | |
| 5,674,240 A | 10/1997 | Bonutti et al. | |
| 5,779,697 A | 7/1998 | Glowa et al. | |
| 5,800,409 A | 9/1998 | Bruce | |
| 5,824,002 A | 10/1998 | Gentelia et al. | |
| 5,882,344 A | 3/1999 | Stouder, Jr. | |
| 5,961,499 A | 10/1999 | Bonutti et al. | |
| 6,197,002 B1* | 3/2001 | Peterson | A61B 17/3462 604/164.01 |
| 6,338,730 B1 | 1/2002 | Bonutti et al. | |
| 6,451,041 B1 | 9/2002 | Moenning et al. | |
| 6,613,038 B2 | 9/2003 | Bonutti et al. | |
| 6,808,492 B2 | 10/2004 | Snyder | |
| 6,814,715 B2 | 11/2004 | Bonutti et al. | |
| 7,413,542 B2 | 8/2008 | Kucklick et al. | |
| 7,435,214 B2 | 10/2008 | Kucklick et al. | |
| 7,445,596 B2 | 11/2008 | Kucklick et al. | |
| 7,473,243 B2 | 1/2009 | Dennis et al. | |
| 7,503,893 B2 | 3/2009 | Kucklick | |
| 7,520,489 B2 | 4/2009 | Rushke et al. | |
| 7,575,565 B2 | 8/2009 | Kucklick | |
| 7,896,897 B2 | 3/2011 | Gresham et al. | |
| 7,993,299 B2 | 8/2011 | Kucklick | |
| 7,998,061 B2 | 8/2011 | Kucklick | |
| 8,012,083 B2 | 9/2011 | Kucklick | |
| 8,025,648 B2 | 9/2011 | Kucklick | |
| 8,038,652 B2 | 10/2011 | Morrison et al. | |
| 8,092,431 B2 | 1/2012 | Lunn et al. | |
| 8,118,731 B2 | 2/2012 | Kucklick | |
| 8,123,676 B2 | 2/2012 | Kucklick | |
| 8,277,418 B2* | 10/2012 | Lopez | A61B 17/3462 604/165.04 |
| 8,298,185 B2 | 10/2012 | Worrel et al. | |
| 8,430,851 B2 | 4/2013 | McGinley et al. | |
| 8,777,902 B2 | 7/2014 | Worrel et al. | |
| 9,119,663 B2 | 9/2015 | Webb | |
| 9,149,294 B2 | 10/2015 | Webb | |
| 9,314,269 B2 | 4/2016 | Webb | |
| 9,398,924 B2 | 7/2016 | Webb | |
| 9,408,631 B2 | 8/2016 | Whittaker et al. | |
| 9,675,379 B2 | 6/2017 | Kucklick | |
| 10,085,768 B2 | 10/2018 | Kucklick | |
| 10,149,699 B2 | 12/2018 | Webb | |
| 10,166,017 B2* | 1/2019 | Schaeffer | A61B 17/3417 |
| 10,258,368 B2 | 4/2019 | Worrel | |
| 10,299,827 B2 | 5/2019 | Dreyfuss | |
| 10,342,577 B2 | 7/2019 | Worrel | |
| 10,813,666 B2 | 10/2020 | Kucklick | |
| 10,856,860 B2 | 12/2020 | Wagner | |
| 2001/0049499 A1 | 12/2001 | Liu et al. | |
| 2005/0059934 A1 | 3/2005 | Wenchell et al. | |
| 2007/0088277 A1 | 4/2007 | McGinley et al. | |
| 2007/0106319 A1 | 5/2007 | Au et al. | |
| 2007/0255218 A1 | 11/2007 | Franer et al. | |
| 2008/0119821 A1 | 5/2008 | Agnihotri et al. | |
| 2008/0294123 A1 | 11/2008 | Lunn et al. | |
| 2009/0030375 A1 | 1/2009 | Franer et al. | |
| 2009/0221968 A1 | 9/2009 | Morrison et al. | |
| 2010/0094227 A1 | 4/2010 | Albretch et al. | |
| 2010/0185058 A1 | 7/2010 | Mastri et al. | |
| 2010/0268241 A1 | 10/2010 | Flom et al. | |
| 2011/0144440 A1 | 6/2011 | Crooper et al. | |
| 2011/0152775 A1 | 6/2011 | Lopez et al. | |
| 2012/0089160 A1 | 4/2012 | Lunn et al. | |
| 2012/0089161 A1 | 4/2012 | Lunn et al. | |
| 2012/0130191 A1 | 5/2012 | Pribanic | |
| 2012/0165611 A1 | 6/2012 | Warren et al. | |
| 2012/0245426 A1 | 9/2012 | Salvas et al. | |
| 2012/0277541 A1 | 11/2012 | Bhargava et al. | |
| 2012/0323081 A1 | 12/2012 | Son | |
| 2013/0190573 A1 | 7/2013 | Smith | |
| 2013/0245381 A1* | 9/2013 | Dang | A61B 17/3423 600/235 |
| 2013/0303858 A1 | 11/2013 | Whittaker et al. | |
| 2013/0317472 A1 | 11/2013 | Finke | |
| 2014/0142394 A1* | 5/2014 | Cataltepe | A61M 25/0102 604/164.11 |
| 2014/0206942 A1 | 7/2014 | Webb | |
| 2014/0207084 A1 | 7/2014 | Webb | |
| 2014/0207100 A1 | 7/2014 | Webb | |
| 2014/0243601 A1* | 8/2014 | Kleyman | A61B 17/0218 600/204 |
| 2015/0257746 A1* | 9/2015 | Seifert | A61B 17/3462 600/206 |
| 2015/0335352 A1 | 11/2015 | Webb | |
| 2016/0183970 A1 | 6/2016 | Webb | |
| 2017/0143326 A1 | 5/2017 | Redler | |
| 2019/0239922 A1 | 8/2019 | Pilgeram et al. | |
| 2019/0365378 A1* | 12/2019 | Heneveld | A61B 17/0482 |
| 2020/0281625 A1 | 9/2020 | Worrel | |

FOREIGN PATENT DOCUMENTS

| | | | |
|---|---|---|---|
| KR | 101090665 B1 | 12/2011 | |
| WO | WO-2011130532 A2 * | 10/2011 | A61B 17/0206 |
| WO | WO2012/044959 | 4/2012 | |

OTHER PUBLICATIONS

AquaLoc Cannula System product brochure, Biomet Sports Medicine, Warsaw IN, 2008, 3 pages. BSM0141.0, REV022908.

Managing fluid and sutures without compromise, Clear-Trac Complete Cannula System product brochure, Smith & Nephew, Inc., Andover, MA, Oct. 2007, 5 pages., 1061531 Rev. C.

Portion of Arthrex product brochure entitled "The Next Generation in Shoulder Repair Technology," Arthrex Inc., 2008, 7 pages.

Cannuflow, Arthroscopy without limits, Products Overview, Cannuflow, 2012, 3 pages., at <<http://www.cannuflow.com/products.html>>.

Caps-Lock cannula product brochure, ArthroCare Sports Medicine, Sunnyvale, CA, 2007, 4 pages, PN AT 50-2009 Rev C.

Dri-Lok Disposable Cannula product sheet, Stryker Corp., Kalamazoo, MI, 1 pg.

Clear Cannula System product information, The new fluid management solution for all your arthroscopic procedures, DePuy Mitek, Inc., Raynham, MA, 2008, 2 pages.

Sportport™ Cannuflow product brochure, "The Easy to Use Super-Flexible Portal Cannula System that Surgeons Have Been Waiting For," Cannuflow Incorporated, 2013, 2 pages.

WECK Vista Teleflex™ brochure, 2012, 6 pages.

International Search Report and Written Opinion issued for PCT Application No. PCT/US2013/068977, dated Jan. 30, 2014, 10 pages.

International Search Report and Written Opinion issued for PCT Application No. PCT/US2013/068978, dated Jan. 30, 2014, 8 pages.

International Search Report and Written Opinion issued for PCT Application No. PCT/US2013/068975, dated Feb. 20, 2014, 8 pages.

Office Action issued for U.S. Appl. No. 13/749,492, dated Dec. 24, 2014, 8 pages.

Office Action issued for U.S. Appl. No. 13/749,496 , dated Jan. 7, 2015, 8 pages.

Notice of Allowance issued for U.S. Appl. No. 13/749,492, dated Apr. 24, 2015, 7 pages.

Office Action issued for U.S. Appl. No. 13/749,496, dated May 13, 2015, 11 pages.

Notice of Allowance issued for U.S. Appl. No. 13/749,492, dated Jul. 21, 2015, 7 pages.

Notice of Allowance issued for U.S. Appl. No. 13/749,496, dated Aug. 5, 2015, 7 pages.

(56) References Cited

OTHER PUBLICATIONS

International Preliminary Report on Patentability (IPRP) issued for PCT Application No. PCT/US2013/068975, dated Aug. 6, 2015, 7 pages.
International Preliminary Report on Patentability (IPRP) issued for PCT Application No. PCT/US2013/068977, dated Aug. 6, 2015, 9 pages.
Office Action for U.S. Appl. No. 13/949,002, dated Sep. 1, 2015, 9 pages.
Notice of Allowance issued for U.S. Appl. No. 13/949,002, dated Dec. 10, 2015, 8 pages.
International Preliminary Report on Patentability issued for PCT Application No. PCT/US2013/068978, dated Feb. 4, 2016, 7 pages.
Notice of Allowance issued for U.S. Appl. No. 14/814,105, dated Mar. 2, 2016, 7 pages.
Office Action for U.S. Appl. No. 15/062,971, dated Apr. 18, 2018, 9 pgs.
Notice of Allowance for U.S. Appl. No. 15/062,971, dated Aug. 3, 2018, 5 pgs.
"GateWay Silicone Cannula Sell Sheet" [retrieved from <<www.sportsmedicine.stryker.com>>], 2019, 2 pages.
"Next Generation in Soft Tissue Repair and Reconstruction" [retrieved from <<https://www.arthrex.com/corporate/virtual-patent-marking>>], 2020, 10 pages.
"ConMed Cannula Portfolio" [retrieved from <<ConMed.com>>, 2015, 8 pages.
"Shoulder and Elbow—Next Generation in Repair and Reconstruction" [retrieved from <<https://www.arthrex.com>>], 2020, 7 pages.

* cited by examiner

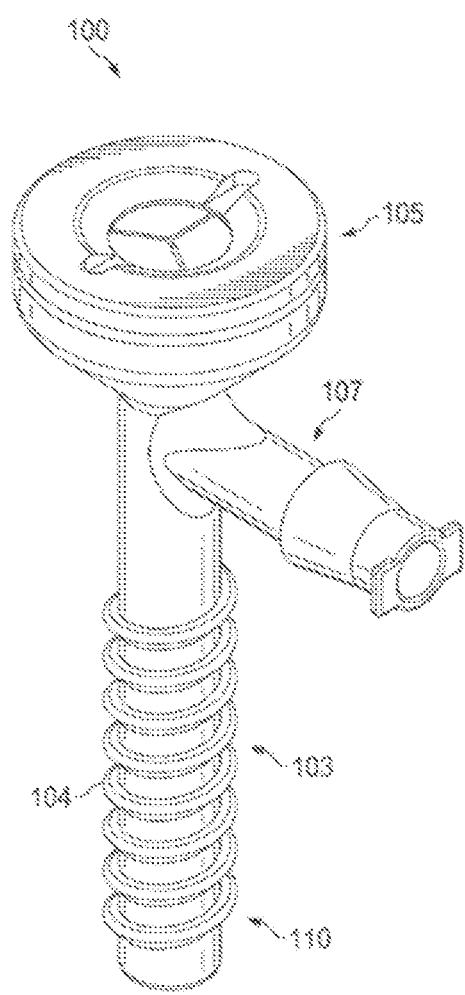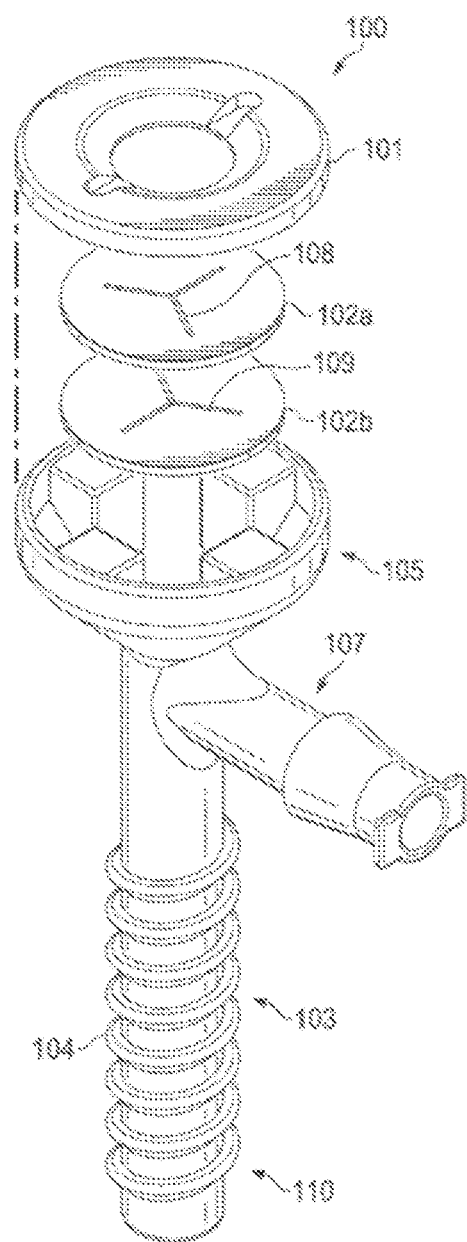
FIG. 1a
(Prior Art)
FIG. 1b
(Prior Art)

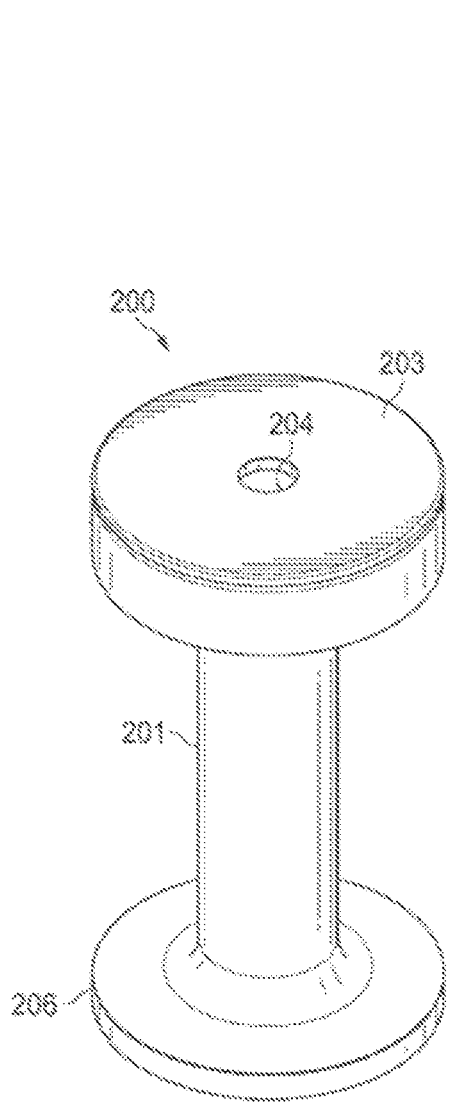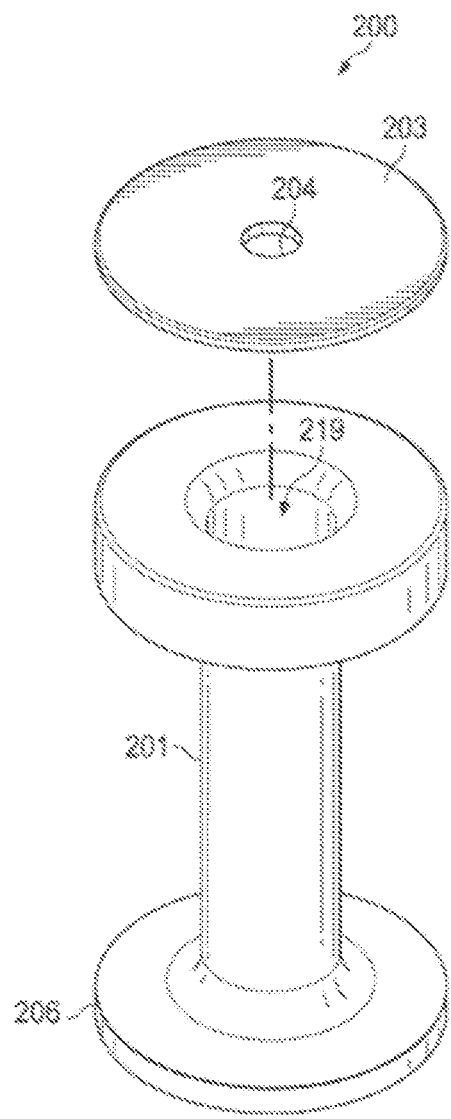
FIG. 2a
(Prior Art)
FIG. 2b
(Prior Art)

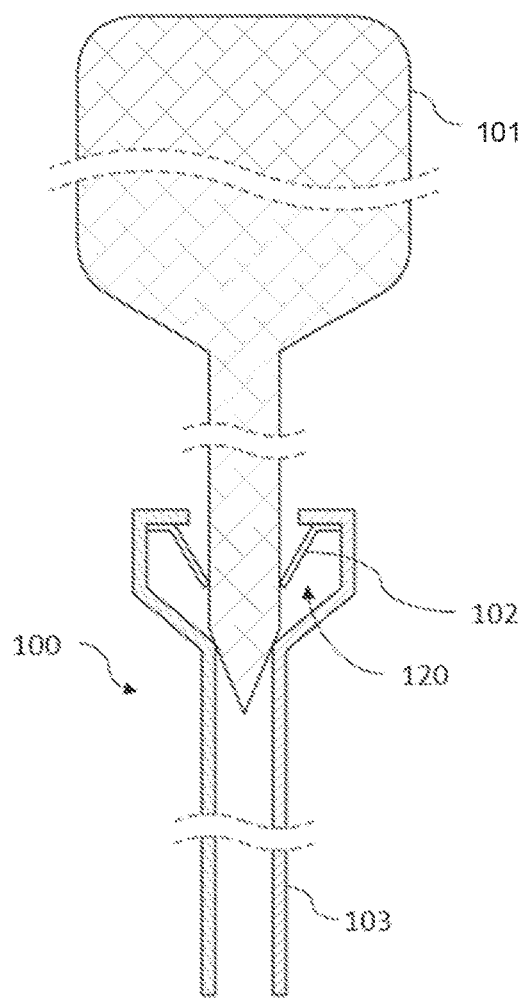
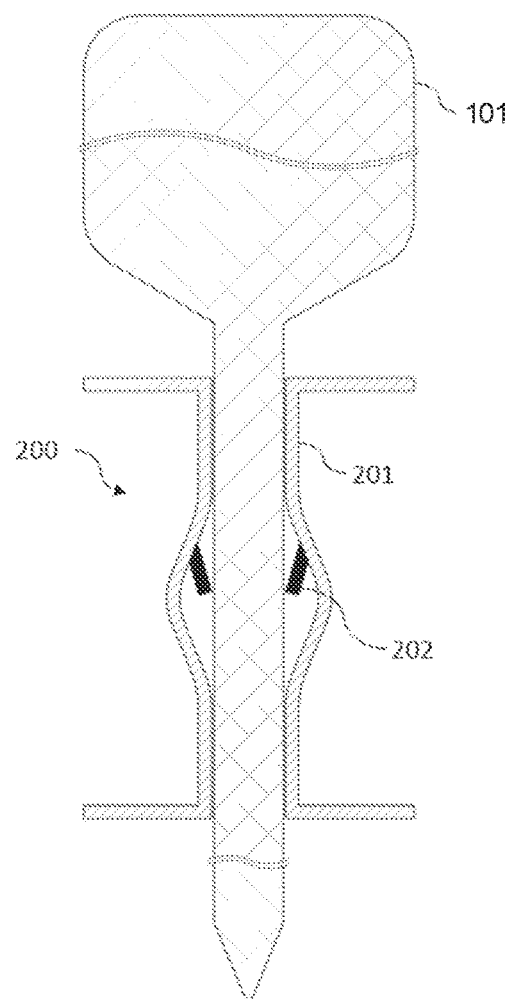
FIG. 4a
(Prior Art)
FIG. 4b
(Prior Art)

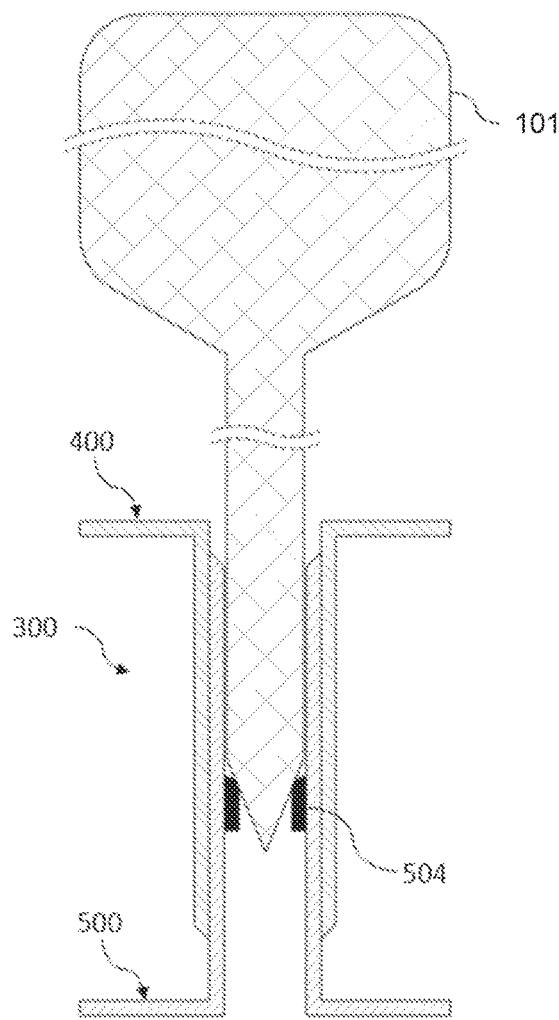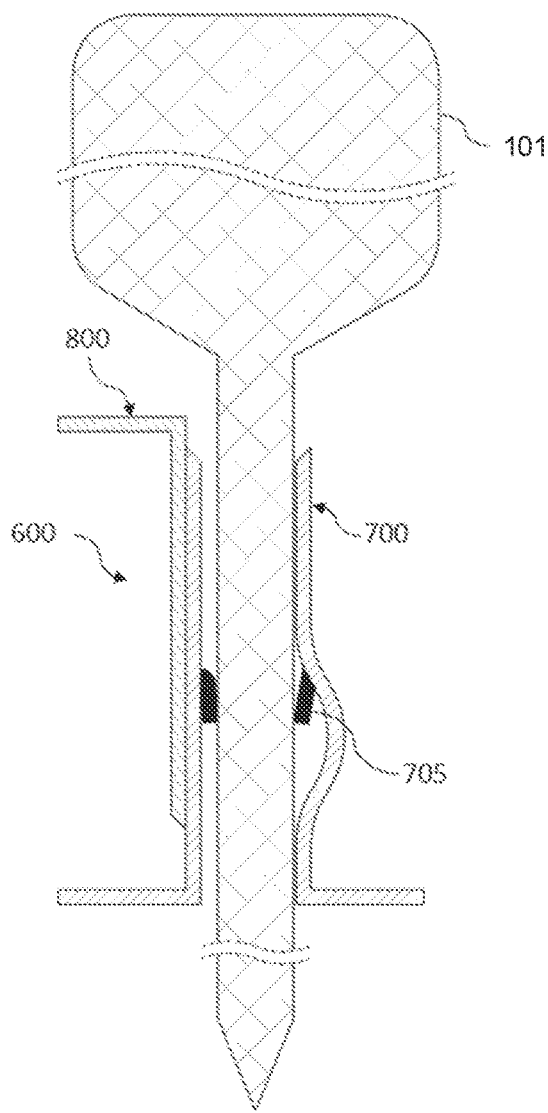
FIG. 4c
(Prior Art)
FIG. 4d

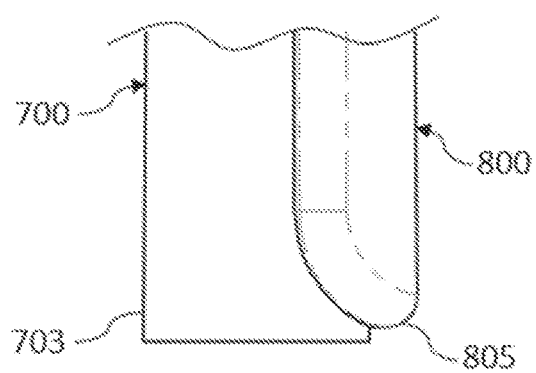
FIG.8a1
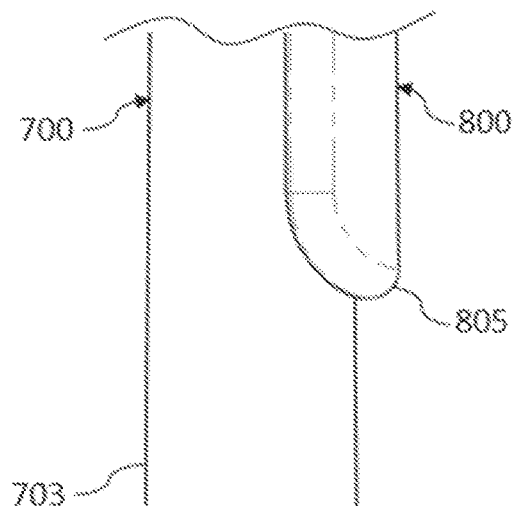
FIG.8b1
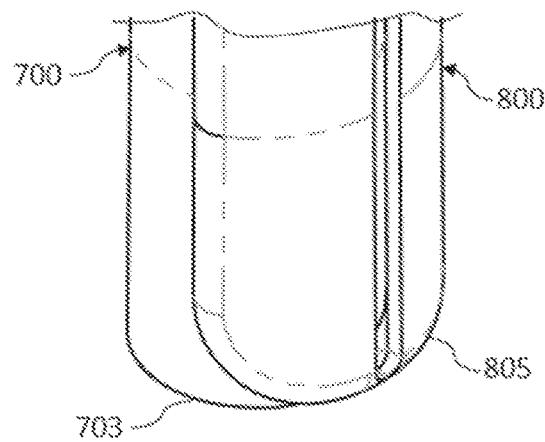
FIG.8a2
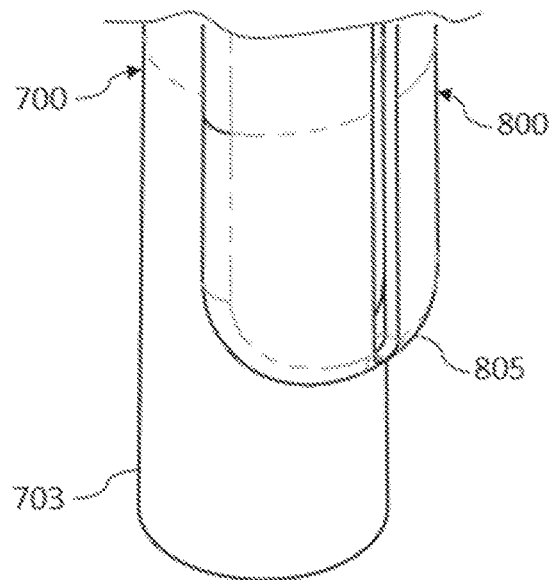
FIG.8b2

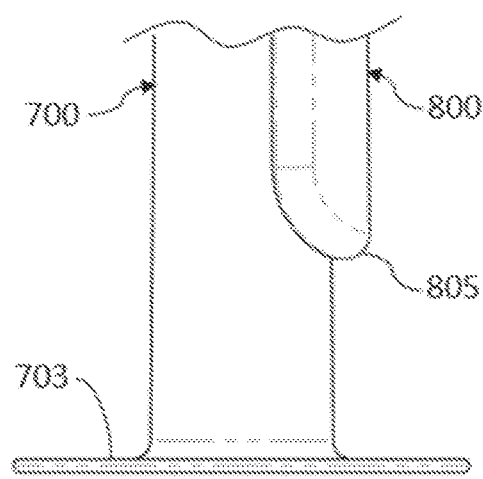
FIG.8c1
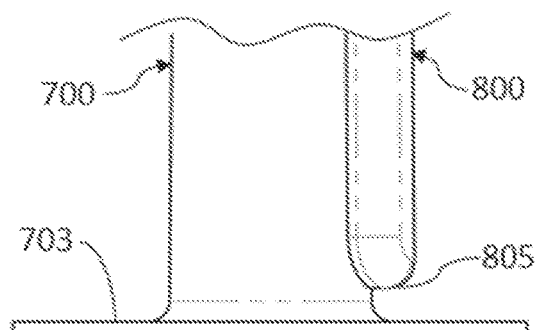
FIG.8d1
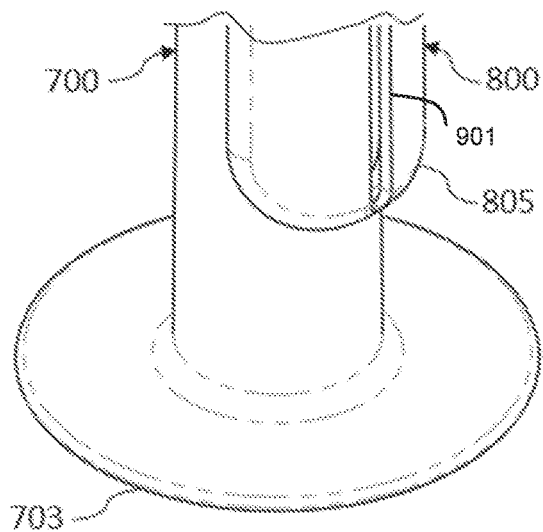
FIG.8c2
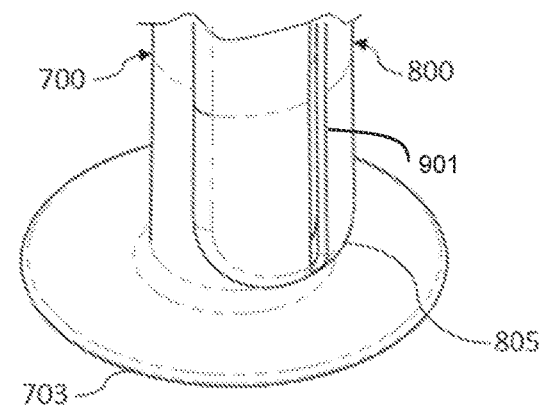
FIG.8d2

HALF PIPE CANNULA AND METHODS OF MANUFACTURING AND USING HALF PIPE CANNULA

CROSS-REFERENCE TO RELATED APPLICATION(S)

This application is a conversion of, and claims a benefit of priority under 35 U.S.C. § 119(e) from, U.S. Provisional Application No. 62/967,960, filed Jan. 30, 2020, entitled "HALF PIPE CANNULA AND METHODS OF MANUFACTURING AND USING HALF PIPE CANNULA," which is fully incorporated by reference herein for all purposes.

TECHNICAL FIELD

This disclosure relates generally to surgical portal devices and, more particularly, to a half pipe cannula having a flexible portion and a rigid portion, the half pipe cannula being useful in minimally invasive surgical procedures, including arthroscopic and endoscopic surgeries.

BACKGROUND

In some cases, it is advantageous to perform a surgery as a minimally invasive surgery (endoscopy or arthroscopy) rather than as an open surgery. Minimally invasive surgeries, such as endoscopy and arthroscopy, are performed through the use of surgical portals (referred to hereinafter as portals). These portals, made through incisions in the skin and some portion of underlying tissue, are used to fill the surgical space with fluid for arthroscopy, and the abdomen with air for endoscopy.

In this disclosure, a non-example of a minimally invasive surgery will be described as it pertains to arthroscopic surgery; however, the disclosure extends into endoscopy as well as arthroscopy. Accordingly, the invention disclosed herein is not limited to arthroscopy.

A cannula is a medical device having an internal passage. A cannula can be inserted into a body, often to create a pathway for elongated instruments to pass into and out of the surgical space. For instance, as alluded to above, during arthroscopy, fluid is directed through a portal into a surgical space (e.g., a patient's shoulder) in order to pressurize and distend the surgical space and improve visualization through an arthroscope. To prevent this fluid from escaping out of the body, a cannula is often inserted into the portal.

The cannula generally consists of a proximal end, an elongated cannulated body having a passage therethrough, and a distal end. When inserted into the portal to the surgical space, the cannula functions to prevent the fluid from escaping from the surgical space, while allowing one or more instruments to be inserted through the passage in the cannula. In some cases, the cannula can prevent the fluid from backing out of the portal regardless of whether an instrument is placed through the cannula. This feature is typically achieved by incorporating one or more flexible dams into the passage in the cannula. Each dam has slits to allow instruments of certain outer diameters to pass through.

FIGS. 1a-1b, 2a-2b, and 3a-3b depict views of an example of prior art cannulas. A traditional cannula, such as cannula 100 depicted in FIGS. 1a-1b, is made of a rigid plastic body 103 and has a proximal end 105, a distal end 110, flexible dams 102a and 102b with slits 108 and 109 located at the proximal end 105 of cannula 100. As shown in FIG. 1b, the flexible dams 102a and 102b are held in place by a cover 101. The rigidity of elongated body 103 allows cannula 100 to be threaded via thread 104 through a portal in the tissue (not shown), typically with the use of an insertion instrument. Because this type of cannula has a large moment arm (e.g., distance from thread 104 to flexible dams 102a and 102b), it has a tendency to tip over when instruments are inserted through it. For this reason, cannula 100 often has to be held in place while inserting instruments through the device, which is not desirable.

FIGS. 2a-2b depict an example of a fully flexible cannula 200. In this case, cannula 200 is entirely made of a flexible material, with a body 201 and a dam (e.g., dam 202 shown in FIG. 4b) incorporated into a passage 219 between the proximal end and the distal end of cannula 200. Generally, the length of cannula 200 is approximately the thickness of the skin and some portion of the underlying tissue. That is, a fully flexible cannula such as cannula 200 shown in FIGS. 2a-2b is usually shorter than a rigid cannula such as cannula 100 shown in FIGS. 1a-1b.

As illustrated in FIGS. 2a-2b, a flexible flange 206 is usually located at the distal end of fully flexible cannula 200. Unlike rigid cannula 100, fully flexible cannula 200 does not have a rigid cover 101. Rather, a thin dam 203 with a small aperture 204 may be attached at the proximal end of cannula 200. This dam can facilitate easier instrument insertion due to less tilting of cannula 200. However, a cannula of such a full flexibility type tends to be more difficult to insert through a portal in the tissue because, as compared to a rigid cannula, a fully flexible cannula tends to deform easier under pressure (e.g., when being inserted into a portal). As such, non-standard instrumentation and/or methods would be required to insert a fully flexible cannula. An example of a non-standard method may involve holding the distal end of a fully flexible cannula with the jaws of a grasping tool, advancing the jaws of the grasping tool and the distal end of the fully flexible cannula together into the portal, and releasing the fully flexible cannula from the grasping tool until after the distal end of the fully flexible cannula exits the portal and can be seen visually by surgical personnel.

In view of the foregoing, there is a need for a new type of cannulas that can overcome the drawbacks of cannulas used in minimally invasive surgical procedures. The invention disclosed herein can address this need and more.

SUMMARY OF THE DISCLOSURE

The disclosed methods and products detailed below serve in part to address the advantages and disadvantages of various types of cannulas. In embodiments disclosed herein, this goal is achieved in a new type of cannula hereinafter referred to as a half pipe cannula.

The half pipe cannula has a first portion and a second portion. The first portion, which includes a proximal end and an elongated tab along the length of the first portion, can be formed from a first material with a selected rigidity. The second portion, which includes a proximal end, a passage, and a distal end, can be formed from a second material with a selected flexibility.

In one embodiment, the second portion may include a dam and a membrane. The dam is located inside the passage and approximately halfway along a length of the half pipe cannula. The membrane is located in the passage near the first portion's proximal flange.

In some embodiments, the second portion of the half pipe cannula extends beyond the distal end of the first portion of the half pipe cannula. In some embodiments, the second portion of the half pipe cannula partially or fully overlaps the elongated tab of the first portion of the half pipe cannula. In some embodiments, the second portion of the half pipe cannula partially or fully overlaps the first portion of the half pipe cannula to include an external thread or bumper feature. In some embodiments, the second portion of the half pipe cannula comprises a flange on a distal end. In some embodiments, the second portion of the half pipe cannula comprises a flange on the proximal end. In some embodiments, the first portion of the half pipe cannula comprises an external thread. In some embodiments, the external thread extends from the proximal end to the distal end of the half pipe cannula. In some embodiments, the second portion of the half pipe cannula comprises thermoplastic elastomer. Numerous other embodiments are also possible.

With a half pipe cannula disclosed herein, an instrument with an outer diameter smaller or larger than the inner diameter of the half pipe cannula can be passed therethrough. For instance, when an instrument having an outer diameter that is larger than the inner diameter of a half pipe cannula is pressed or otherwise advanced through the elongated body of the half pipe cannula, because the rigid portion of the half pipe cannula only partially wraps around the circumference of the half pipe cannula, the flexible portion of the half pipe cannula can allow the elongated body and the dam therein to expand outward radially, allowing the instrument to pass through.

These, and other, aspects of the disclosure will be better appreciated and understood when considered in conjunction with the following description and the accompanying drawings. It should be understood, however, that the following description, while indicating various embodiments of the disclosure and numerous specific details thereof, is given by way of illustration and not of limitation. Many substitutions, modifications, additions, and/or rearrangements may be made within the scope of the disclosure without departing from the spirit thereof, and the disclosure includes all such substitutions, modifications, additions, and/or rearrangements.

BRIEF DESCRIPTION OF THE DRAWINGS

The drawings accompanying and forming part of this specification are included to depict certain aspects of the invention. A clearer impression of the invention, and of the components and operation of systems provided with the invention, will become more readily apparent by referring to the exemplary, and therefore non-limiting, embodiments illustrated in the drawings, wherein identical reference numerals designate the same components. Note that the features illustrated in the drawings are not necessarily drawn to scale.

FIG. 1a depicts an example of a rigid cannula.

FIG. 1b depicts the rigid cannula of FIG. 1a in an exploded view.

FIG. 2a depicts an example of a fully flexible cannula.

FIG. 2b depicts the fully flexible cannula of FIG. 2a in an exploded view.

FIG. 3b depicts a cross-sectional view of the hybrid cannula of FIG. 3a.

FIG. 4a depicts a cross-sectional view of a large instrument being inserted into a rigid cannula.

FIG. 4b depicts a cross-sectional view of a large instrument being inserted into a flexible cannula.

FIG. 4c depicts a cross-sectional view of a large instrument being inserted into a hybrid cannula.

FIG. 4d depicts a cross-sectional view of a large instrument being inserted into an example of a half pipe cannula according to some embodiments disclosed herein.

FIG. 5b depicts a perspective view of the half pipe cannula of FIG. 5a.

FIG. 5c depicts a cross-sectional view of the half pipe cannula of FIG. 5a.

FIG. 8a1 depicts a side view of the distal end of an example of a half pipe cannula according to some embodiments disclosed herein.

FIG. 8a2 depicts a perspective view of the half pipe cannula of FIG. 8a1.

FIG. 8b1 depicts a side view of the distal end of an example of a half pipe cannula according to some embodiments disclosed herein.

FIG. 8b2 depicts a perspective view of the half pipe cannula of FIG. 8b1.

FIG. 8c1 depicts a side view of the distal end of an example of a half pipe cannula according to some embodiments disclosed herein.

FIG. 8c2 depicts a perspective view of the half pipe cannula of FIG. 8c1.

FIG. 8d1 depicts a side view of the distal end of an example of a half pipe cannula according to some embodiments disclosed herein.

FIG. 8d2 depicts a perspective view of the half pipe cannula of FIG. 8d1.

FIG. 10b depicts a cross-sectional view of the half pipe cannula of FIG. 10a.

FIG. 11a depicts an exploded view of another example of a half pipe cannula according to some embodiments disclosed herein.

FIG. 11b depicts a side view of the half pipe cannula of FIG. 11a.

FIG. 12b depicts a side view of the half pipe cannula of FIG. 12a.

FIG. 13b depicts a flexible portion of the half pipe cannula of FIG. 13a.

FIG. 13c depicts a rigid portion of the half pipe cannula of FIG. 13a.

DETAILED DESCRIPTION

Figure 3A:
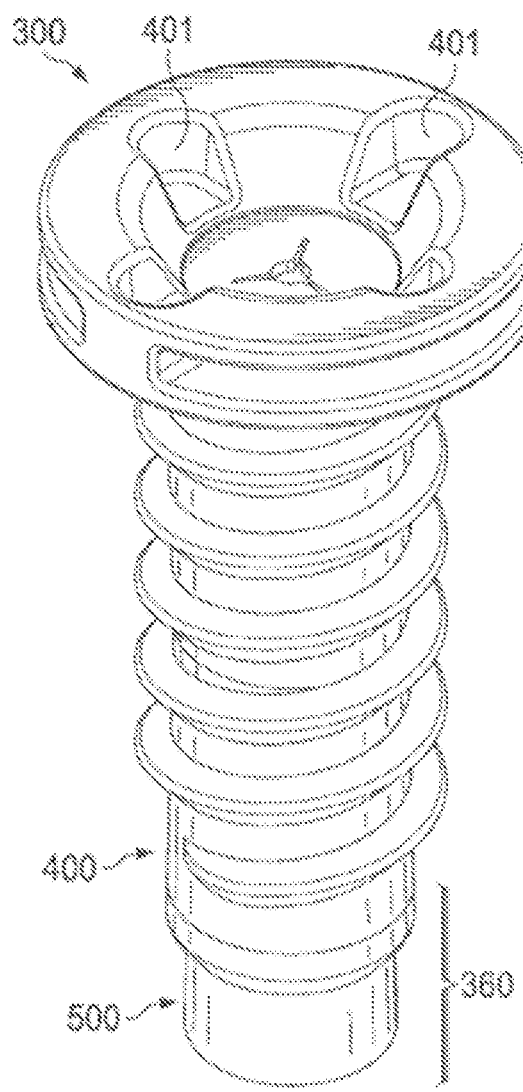
FIG. 3a depicts an example of a hybrid cannula.

Embodiments disclosed herein provide a new type of surgical device that can overcome the shortcomings of various types of cannulas. Referred to herein as half pipe cannulas, the new type of surgical device has the ability, among others, to prevent tipping over during instrument insertion similar to a fully flexible cannula and may be able to be inserted through a portal using traditional methods similar to a rigid cannula. Additionally, a half pipe cannula disclosed herein can allow for some instruments having an outer diameter larger than the inner diameter of the half pipe cannula to pass through. Those skilled in the art will recognize that the invention can be used in arthroscopic as well as endoscopic surgeries without departing from the spirit or scope of the invention.

Before describing embodiments of a half pipe cannula in detail, an overview of various types of cannulas might be helpful. As discussed above, FIG. 1a shows a fully assembled rigid cannula 100 that is typically used in arthroscopic surgeries. An exploded view of cannula 100 is shown in FIG. 1b. Generally, cannula 100 consists of a distal end 110, an elongated body 103 with thread 104, proximal end 105, and dams 102a and 102b disposed at the proximal end 105 and held together by a cover 101.

FIG. 2a depicts another type of cannulas typically used in arthroscopic surgeries. As discussed above, cannula 200 may be entirely flexible and have flanges on both ends. An exploded view of cannula 200 is depicted in FIG. 2b, showing components of fully flexible cannula 200. The entire cannula 200 is typically made from the same material, which may be a flexible rubber, silicone, or the like. That is, elongated body 201, thin membrane 203, and the proximal and distal flanges of cannula 200 are typically made of the same material. Not shown in FIGS. 2a and 2b is a dam positioned inside passage 219 of elongated body 201.

Fully flexible cannula 200 can be characterized as having several disadvantages. Some of these disadvantages include cannula 200 may be too flexible for use with traditional insertion procedures, cannula 200 may slip and move up and down within a portal during instrument insertion and/or removal, and so on. However, a distinct advantage of a fully flexible cannula is that, because of its flexible nature, a fully flexible cannula can allow for passage of non-standard objects, such as tissue grafts and large diameter instruments, which are otherwise difficult to pass through when rigid cannulas are used. Another advantage is that, due to the location of a dam within the passage, ease of instrument insertion using a fully flexible cannula is improved over a rigid cannula which has dams loaded at the proximal end thereof.

In recent years, a new type of cannula that leverages the advantages of a rigid cannula and a fully flexible cannula has been developed. For example, U.S. Pat. No. 9,398,924 provides a hybrid cannula with a rigid portion overmolded to a flexible portion, as illustrated in FIGS. 3a-3b.

FIG. 3a depicts an example of a hybrid cannula 300 which has a rigid elongated body 400, a flexible portion 500, a thin membrane 502, and a flexible dam 504. Flexible portion 500 is overmolded or otherwise affixed to rigid portion 400, allowing hybrid cannula 300 to combine features of rigid cannula 100 and flexible cannula 200.

Figure 3B:
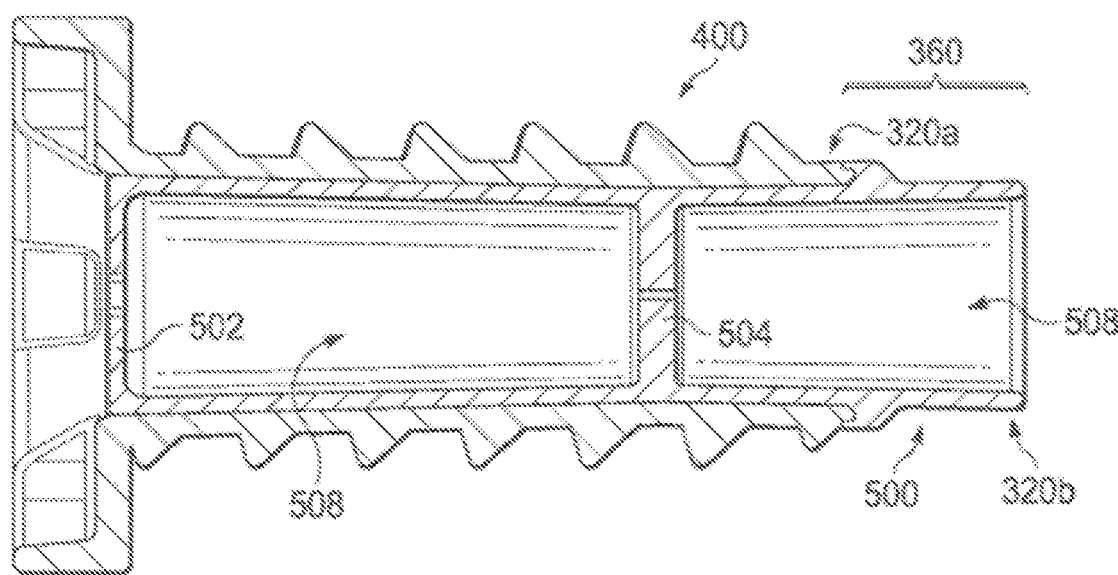

FIG. 3b depicts a cross-sectional view of hybrid cannula 300. As shown in FIG. 3b, rigid portion 400 has an elongated body and a proximal flange, while flexible portion 500 has a flexible dam 504 within a passage 508 and a flexible distal tip 360. Flexible dam 504 is incorporated between the proximal end and the distal end of hybrid cannula 300 within passage 508. Distal tip 360 of flexible portion 500 has a distal end 320b that extends beyond a distal end 320a of rigid portion 400. Distal tip 360 of flexible portion 500 may be flexible, semi-rigid, transparent, or have some other characteristic that is different than distal end 320a. Hybrid cannula 300 may be inserted through a portal in the tissue using traditional instrumentation (e.g., via features 401), similar to cannula 100 shown in FIGS. 1a-1b. Further, flexible portion 500 of hybrid cannula 300 provides for unique distal tips that allow for easier instrument maneuverability over rigid cannula 100, similar to fully flexible cannula 200 depicted in FIGS. 2a-2b.

Compared with fully flexible cannula 200, rigid cannula 100 and hybrid cannula 300 can be characterized as having a particular disadvantage. In each of these types of cannulas, because of a rigid body (e.g., elongated body 103 of rigid cannula 100) or a rigid portion (e.g., rigid portion 400 of hybrid cannula 300) that restricts radial expansion, passage of a non-standard object may not be possible. However, at times, it might be necessary to insert such a non-standard object through a cannula. As compared with normal cannula use, such an object can be difficult to pass through the cannula due to size and/or shape (e.g., if the outer diameter of an instrument is larger than the inner diameter of a respective cannula). Non-limiting examples of objects that might need to be inserted (all at once or one at a time) through a cannula can include, but are not limited to, tissue grafts, large diameter instruments, multiple instruments, and so on. In certain procedures that require such non-standard object(s), rigid cannula 100 and hybrid cannula 300 cannot be used. To illustrate the different responses in allowing or preventing passage of a large instrument, views of different types of cannulas during instrument insertion are depicted in FIGS. 4a-4c.

FIG. 4a shows rigid cannula 100 from FIGS. 1a-b in which dam 102 flexes down into a bulbous space 120 at the proximal end of rigid cannula 100, allowing large instrument 101 to pass towards the rigid elongated body 103. However, because the instrument's outer diameter is larger than the inner diameter of the rigid elongated body 103, large instrument 101 cannot pass through the rigid elongated body 103 of rigid cannula 100.

FIG. 4b shows fully flexible cannula 200 from FIGS. 2a-2b with large instrument 101 passing through a flexible elongated body 201 and pushing through dam 202. At the location of dam 202, because the entire body of fully flexible cannula 200 is flexible, the inner diameter of the flexible elongated body 201 of fully flexible cannula 200 can expand radially to allow for passage of large instrument 101. In some cases, the outer diameter of large instrument 101 may be larger than the inner diameter of the flexible elongated body 201. However, large instrument 101 can still be passed through fully flexible cannula 200 because both the flexible elongated body 201 and dam 202 can expand radially to accommodate the larger outer diameter of large instrument 101, allowing large instrument 101 to pass through.

FIG. 4c depicts an attempt to pass large instrument 101 through hybrid cannula 300 from FIGS. 3a-b. In this case, the elongated body of hybrid cannula 300, which consists of a rigid portion 400 and a flexible portion 500, does not allow large instrument 101 to pass through dam 504 because rigid portion 400, which surrounds flexible portion 500 and dam 504, constrains and prevents dam 504 from expanding radially. Instead, as large instrument 101 is advanced inside the elongated body of hybrid cannula 300, the distal tip of large instrument 101 exerts pressure radially onto dam 504, causing dam 504 to fold over which, in turn, decreases the inner diameter of the elongated body of hybrid cannula 300. Accordingly, if an instrument's outer diameter is greater than the inner diameter of the elongated body of hybrid cannula 300, then the instrument cannot be passed through hybrid cannula 300.

Furthermore, rigid cannula 100, flexible cannula 200, and hybrid cannula 300 all have a similar disadvantage during insertion through a portal in the soft tissue. Each of these types of cannulas requires the use of an additional instrument to push or pull the distal tip of a cannula through the portal towards the surgical site. The use of this additional instrument adds time to the operating procedure, increases the packaging size, and thus the storage space of the product, and may necessitate sterilizing the insertion instrument for each new patient.

In view of the foregoing, there is a need for a new type of cannulas that can overcome the drawbacks of various types of cannulas used in minimally invasive surgical procedures. To this end, a goal of the invention disclosed herein is to leverage certain advantageous characteristics of rigid cannula 100, fully flexible cannula 200, and hybrid cannula 300 in providing a new type of cannulas which incorporate beneficial features of rigid cannula 100, flexible cannula 200, and hybrid cannula 300 without their respective drawbacks. In embodiments disclosed herein, this goal is achieved in a half pipe cannula that has a flexible elongated body with a partially wrapped rigid section. The half pipe cannula has the ability, among others, to remain stable during instrument insertion, be inserted using traditional methods or possibly no instrument at all, and can allow instruments that are otherwise difficult to insert to pass through the cannula. The partially wrapped rigid section of the half pipe cannula provides the support needed for insertion through soft tissue, possibly without the aid of an insertion instrument, while the flexible elongated body with flexible distal features allows for passage of standard instruments and passage of non-standard instruments and/or objects, thereby improving the efficiency of an operating procedure, including possibly reducing the time and/or instrumentation needed to prepare a surgical site for operation.

FIG. 4d shows an example of how an instrument with an outer diameter larger than the inner diameter of a half pipe cannula can be passed through the half pipe cannula. In the example of FIG. 4d, the outer diameter of large instrument 101 is larger than the inner diameter of half pipe cannula 600 prior to insertion of large instrument 101. Half pipe cannula 600 has a dam 705 and an elongated body composed of a flexible portion 700 and a rigid portion 800. As illustrated in FIG. 4d, rigid portion 800 only partially wraps around the circumference of half pipe cannula 600. When large instrument 101 is pressed or otherwise advanced through the elongated body of half pipe cannula 600, flexible portion 700 of half pipe cannula 600 allows the elongated body and dam 705 to expand outward radially, allowing large instrument 101 to pass through half pipe cannula 600, as shown in FIG. 4d. Embodiments of a half pipe cannula disclosed herein can be implemented in various ways, some examples of which will now be described in more detail below.

Figure 5A:
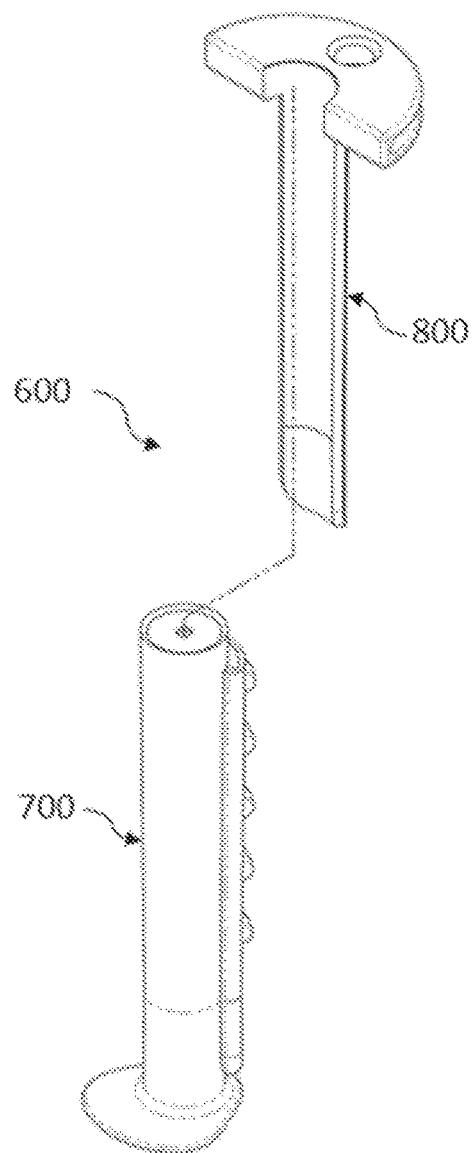
FIG. 5a depicts an exploded view showing portions of an example of a half pipe cannula according to some embodiments disclosed herein.
Figure 5B:
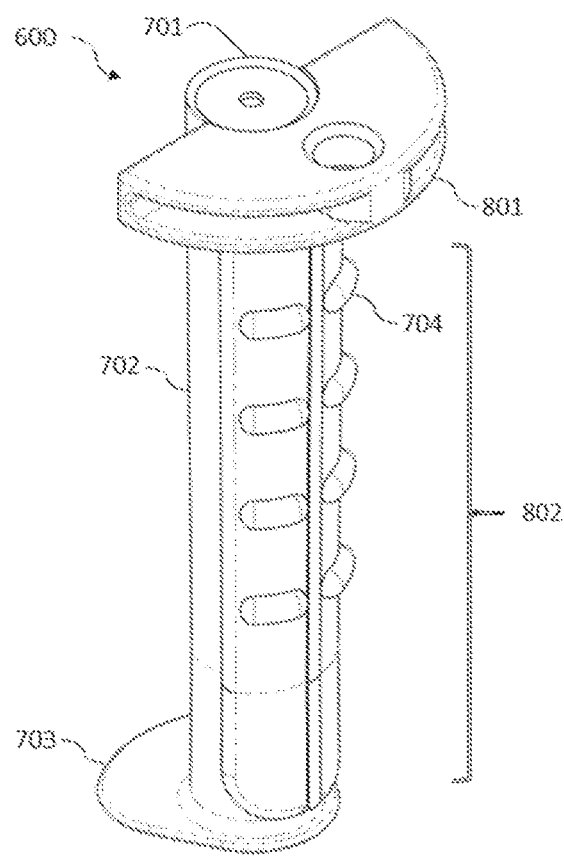
Figure 5C:
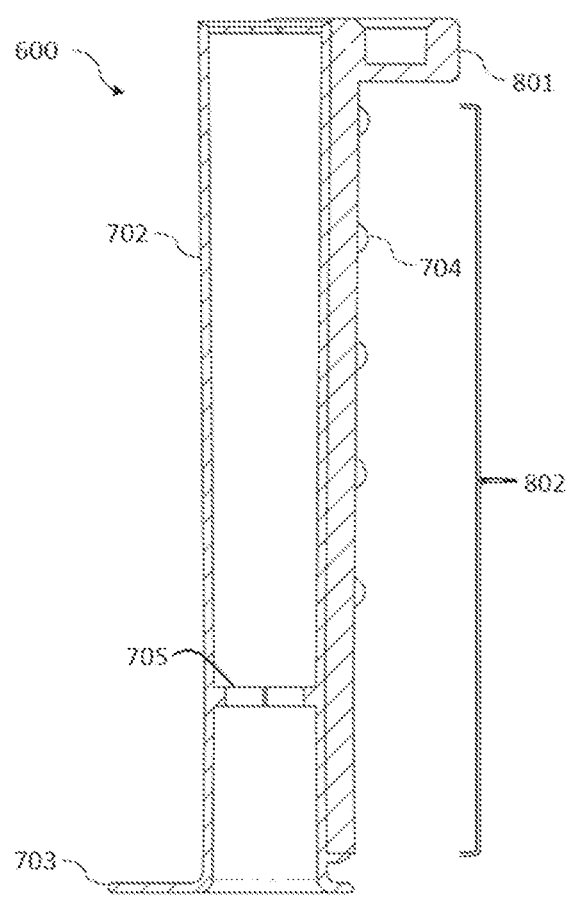

FIGS. 5a-5c depict an example of a half pipe cannula 600 according to some embodiments disclosed herein. As illustrated in FIGS. 5a-5c, a half pipe cannula 600 is made of a flexible portion 700 and a rigid portion 800. Flexible portion 700 may have a proximal end 701, an elongated body 702 with an inner passage, interior dam 705, and a distal end 703. Rigid portion 800 may have a proximal end 801 and an elongated tab 802. Rigid elongated tab 802 does not fully wrap around the outer diameter of elongated body 702 of flexible portion 700. It is appreciated that half pipe cannula 600 can have a number of variations of these features according to some embodiments.

The flexible portion and the rigid portion of such a half pipe cannula together provide a structural property that allows the half pipe cannula to be inserted through a portal in the tissue, possibly without the aid of any instrument. More specifically, the flexible and rigid portions of the elongated body may work together to pull the flexible distal tip thereof through the portal using the rigid elongated tab. During insertion, the flexible elongated body may compress against the elongated tab to conform to the size and/or shape of the portal incision and allow for easy passage of the half pipe cannula through the portal. This property would be advantageous in a surgical setting as it would eliminate the step required to insert and remove an insertion instrument from the half pipe cannula during cannula insertion through the portal. This advantage is evident to those skilled in the art of the invention.

As discussed above, half pipe cannula 600 may comprise a flexible portion 700 with a dam and/or membrane in an internal passage, and a rigid portion 800 which includes a proximal flange 801 and an elongated tab 802. Flexible portion 700 is affixed, adhered, glued, bonded, overmolded, or otherwise attached to rigid portion 800. Flexible portion 700 has a fully enclosed internal passage while the rigid portion's elongated tab 802 does not fully wrap around the flexible portion. Elongated body 702 of flexible portion 700 may include one or more features such as threads 704 that partially or fully cover elongated tab 802 of rigid portion 800, as shown in FIGS. 5a-5b, and that are structured to prevent the cannula from moving into and out of the portal during instrument insertion and removal. More specifically, the flexible and rigid portions of the elongated body may work together to stabilize the half pipe cannula during insertion and removal such that the half pipe cannula does not slide in and out of the portal or tilt over. As shown in FIG. 5c, flexible portion 700 may include a dam 705 and a passage to allow instruments to pass through during arthroscopy, while rigid portion 800 may have a proximal flange 801, elongated tab 802, and threads (not shown).

In embodiments, the flexible portion of a half pipe cannula disclosed herein may be composed of one material or several materials. Additionally, each feature of the flexible portion of the half pipe cannula may be made of only one material or of several materials. The materials of each feature may be flexible or semi-flexible.

Examples of flexible materials that may be used in the flexible portion of the half pipe cannula may be appropriate for use in surgery and may include, but are not limited to, silicone, thermoplastic elastomer, polyurethane, and rubber. For both flexible and semi-flexible materials, it may be beneficial for the material to include colorants and/or to be partially transparent or translucent.

In embodiments, the rigid portion of the half pipe cannula disclosed herein may be composed of one material or several materials. Additionally, each feature of the rigid portion of the half pipe cannula may be made of only one material or of several materials. The materials of each feature may be rigid or semi-rigid.

Examples of rigid materials that may be used in the rigid portion of the half pipe cannula and may be appropriate for use in surgery may include, but are not limited to polycarbonate, polyetheretherketone (PEEK), acrylonitrile butadiene styrene (ABS), aluminum, stainless steel, and titanium.

Some embodiments of a half pipe cannula disclosed herein can be lighter in weight than a conventional cannula, such as rigid cannula 100. The reduction in weight of half pipe cannula 600 relative to rigid cannula 100 can be due to the elimination and/or size reduction of one or more features of rigid cannula 100. For example, half pipe cannula 600 may not include a stop cock such as stop cock 107 of rigid cannula 100. As another example, selected for the same patient, half pipe cannula 600 may be shorter in length relative to rigid cannula 100.

In some embodiments, a half pipe cannula disclosed herein may be manufactured to a number of different overall lengths. A correctly sized length of a half pipe cannula can be selected for use during the arthroscopy based on the thickness of the soft tissues through which the portal extends.

As discussed above with reference to FIGS. 4a-4c, the results of trying to insert large instrument 101 through a cannula may vary from cannula type to cannula type. As illustrated in FIG. 4d, the same large instrument 101 can pass through half pipe cannula 600, even though the outer diameter of large instrument 101 is larger than the inner diameter of the passage of half pipe cannula 600.

Attention is now turned to insertion of a half pipe cannula through a soft tissue portal according to some embodiments disclosed herein. As described above, all types of cannulas are generally inserted into the body through the use of some type of instrumentation. Some examples of these instruments are obturators, switching sticks, hemostats, and cannula-specific reusable instruments. A half pipe cannula disclosed herein may have the distinct advantage of being able to be inserted into the body without the use of any instrumentation. Below describes an example of a process of inserting an example embodiment of a half pipe cannula into the body.

Prior to inserting a half pipe cannula (e.g., half pipe cannula 600), a surgeon makes a small incision into the skin. Next, the surgeon grasps, with his or her hand, the rigid portion of the half pipe cannula and place the distal tip of the half pipe cannula to the incision site.

As the surgeon applies a force along the longitudinal axis of the half pipe cannula, the rigid portion of the distal tip may begin to slide through the incision since its width is smaller than the incision. At this point, the flexible portion of the distal tip will fold around the rigid elongated tab. As the flexible portion of the distal tip folds up, it may settle tightly along the profile of the elongated tab and thus reduce the overall profile of the flexible portion so that it fits through the incision.

As the rigid portion of the distal tip progresses through the incision site, it pulls the flexible portion of the distal tip with it and forces it to conform to the profile of the incision. As the rigid portion of the distal tip reaches some distance past the soft tissue and into the surgical space, the flexible portion of the distal tip passes through the soft tissue portal and is free to expand back to its original shape.

In this way, a flexible distal flange and/or elongated tip with a larger profile than an incision may be passed through the incision without the use of additional insertion instrumentation. At this point, the elongated body of the flexible portion of the cannula may reform its profile so that the soft tissue portal is filled by the flexible portion of the half pipe cannula. In some applications, this method is sufficient for inserting the half pipe cannula through the portal; however, this method does not preclude instrumentation from being used to guide the half pipe cannula through the portal in circumstances when it is necessary to do so. In some cases, it may be beneficial to dilate the portal with instrumentation prior to inserting the half pipe cannula through the portal.

Attention will now be directed to embodiments having variations of features which can be made as part of the half pipe cannula. Some of these features may include an elongated tab, proximal end, distal end, threads, and so on.

Figure 6A:
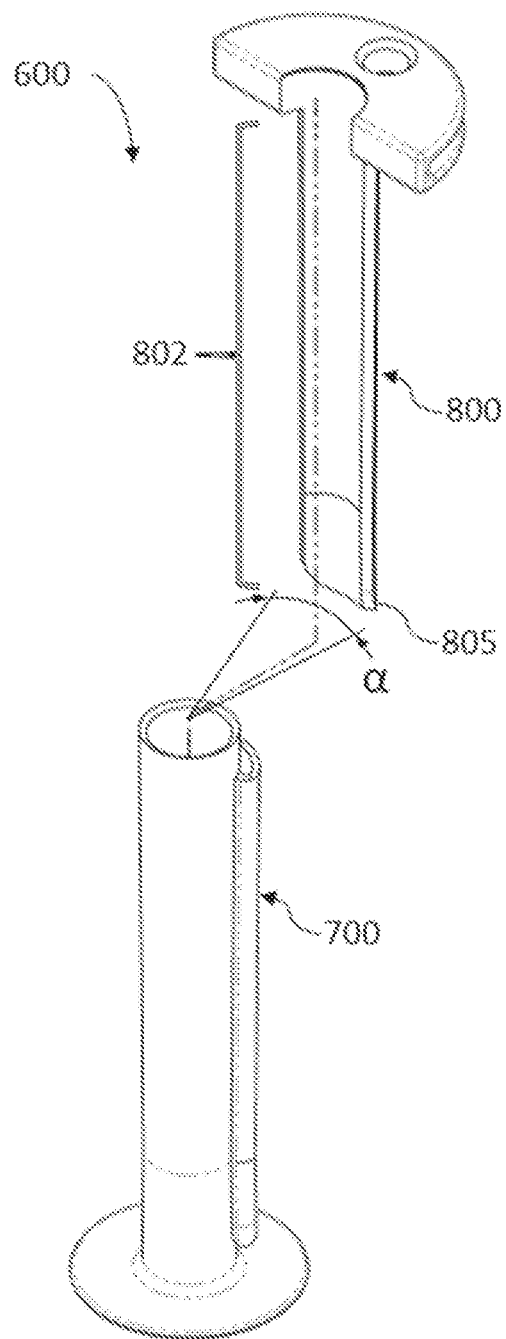
FIG. 6a depicts an exploded view showing portions of an example of a half pipe cannula according to some embodiments disclosed herein.
Figure 6B:
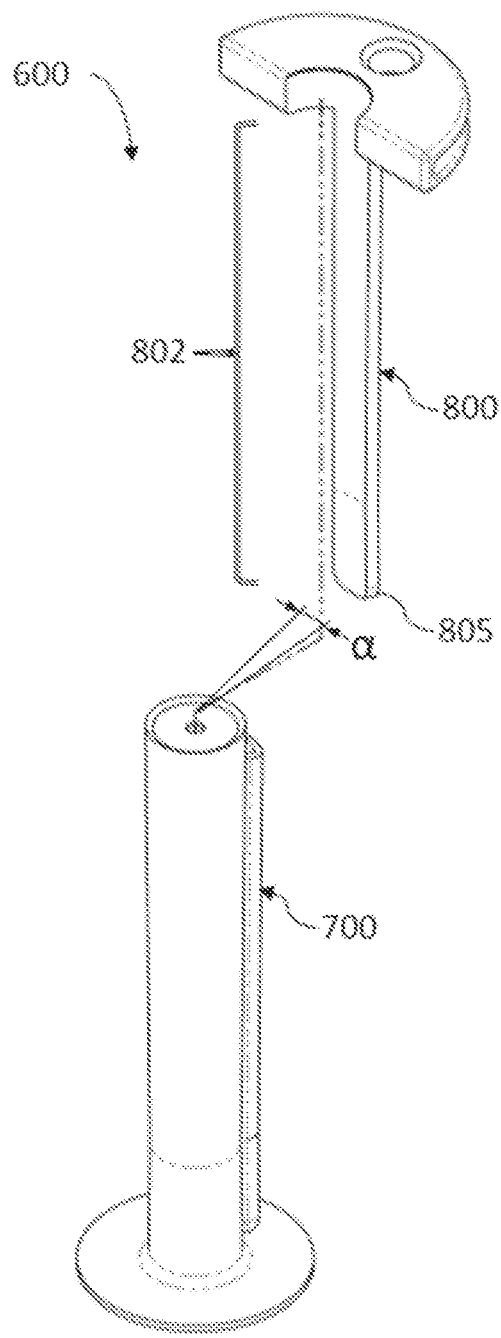
FIG. 6b depicts an exploded view showing portions of another example of a half pipe cannula according to some embodiments disclosed herein.

FIGS. 6a-6b show exploded views depicting portions of two embodiments of half pipe cannula 600. As shown in FIGS. 6a and 6b, while both embodiments of half pipe cannula 600 have a rigid portion 800 with an elongated tab 802 which does not fully wrap around flexible portion 700, they differ in the central angle $\alpha$ and hence arc length of elongated tab 802. The central angle $\alpha$ of elongated tab 802 in FIG. 6a is approximately 60 degrees and the central angle $\alpha$ of elongated tab 802 in FIG. 6b is approximately 30 degrees. One skilled in the art would anticipate that this central angle could be any value but would likely range from 30 degrees to 270 degrees. In some embodiments, the preferred range of the central angle $\alpha$ of elongated tab 802 is approximately 130 degrees.

Figure 6C:
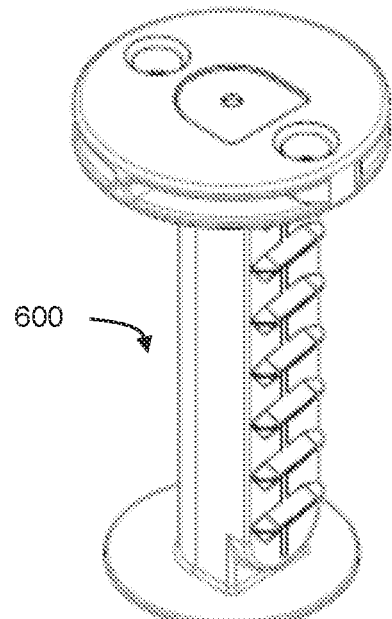
FIG. 6c depicts a perspective view of an example of a half pipe cannula having an asymmetric cross-sectional profile according to some embodiments disclosed herein.
Figures 6D, 6E:
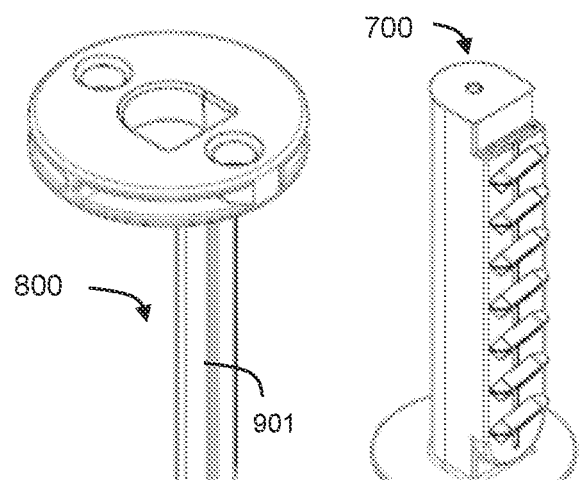
FIG. 6d depicts a perspective view of a rigid portion of the half pipe cannula of FIG. 6c.
FIG. 6e depicts a perspective view of a flexible portion of the half pipe cannula of FIG. 6c.

In some embodiments, a half pipe cannula may have an elongated tab that have a non-curved profile. That is, the elongated tab would not be circular but straight (and hence creating a D-shaped half pipe cannula profile). FIG. 6c depicts a perspective view of an example of a half pipe cannula having an asymmetric cross-sectional profile according to some embodiments disclosed herein. FIG. 6d depicts a perspective view of a rigid portion of the half pipe cannula of FIG. 6c. FIG. 6e depicts a perspective view of a flexible portion of the half pipe cannula of FIG. 6c. As exemplified in FIGS. 6c-6e, with an asymmetric cross-sectional profile, the central angle $\alpha$ of the elongated tab of rigid portion 800 would not vary, but the width of the elongated tab may vary.

In some embodiments, it is advantageous to make the central angle $\alpha$ or width of the elongated tab of rigid portion 800 as small as possible to allow for the elongated tab to more easily be pushed through the soft tissue portal. The smaller the central angle α or width of the elongated tab is, the smaller the incision size can be on the patient. Conversely, the elongated tab 802 must be strong enough to resist forces placed on it during insertion through the soft tissue portal without breaking. This may mean that, depending upon application, the central angle α or width and thickness of the elongated tab of a half pipe cannula may need to be optimized, that structural ridges (e.g., ridge 901 shown in FIG. 6d) may need to be placed along the length or width of the elongated tab, that threads may need to be added to the elongated tab, and/or other geometric stability features may need to be added to the half pipe cannula to protect its elongated tab.

It may also be advantageous for the central angle α or width and/or thickness of the elongated tab to vary along the length of the elongated tab. To this end, FIGS. 6a-6b show that elongated tab 802 of rigid portion 800 can have a distal tip 805 that is tapered to a smaller width, have rounded edges, and/or have a spoon-like feature which can also aid in easing insertion of half pipe cannula 600 into the soft tissue portal. In some embodiments, distal tip 805 could taper to a point so that no surface of the distal tip 805 is perpendicular to the longitudinal axis of half pipe cannula 600.

FIGS. 7a-7d show embodiments of half pipe cannula 600 with various proximal features, including variations of flanges. These flanges may function to aid in inserting half pipe cannula 600 through the soft tissue portal and/or to prevent half pipe cannula 600 from pushing all the way through the soft tissue portal into the surgical space.

Figure 7A:
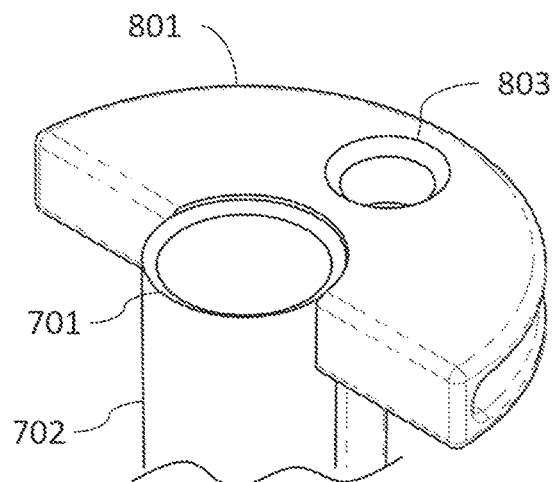
FIG. 7a depicts the proximal end of an example of a half pipe cannula according to some embodiments disclosed herein.

FIG. 7a shows an embodiment of half pipe cannula 600 having a rigid flange 801 which only wraps partially around a flexible proximal tip 701 and a flexible elongated body 702. In this embodiment, rigid flange 801 wraps approximately 180 degrees around flexible proximal tip 701 and flexible elongated body 702. In some embodiments, rigid flange 801 could wrap any amount around flexible proximal tip 701 and flexible elongated body 702, for instance, in the range of approximately 15 degrees to 360 degrees.

In some embodiments, it may be advantageous for rigid flange 801 to contain features structured for engagement with insertion instruments in cases where it is too difficult to insert a half pipe cannula through a soft tissue portal by hand. One example of an engagement feature 803 is depicted in the embodiments of half pipe cannula 600 shown in FIGS. 7a and 7b. Engagement feature 803 can be implemented in many ways, including, but are not limited to, a hole, half hole, slot, boss, or any number of shapes.

Figure 7C:
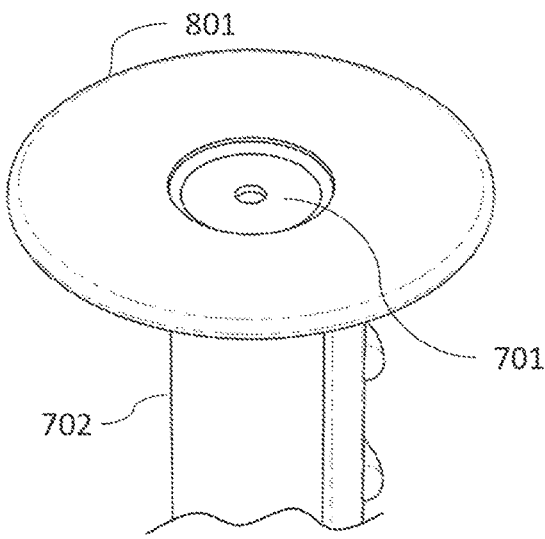
FIG. 7c depicts the proximal end of an example of a half pipe cannula according to some embodiments disclosed herein.
Figure 7B:
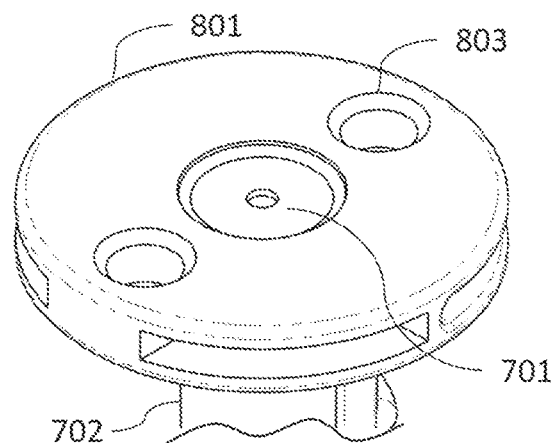
FIG. 7b depicts the proximal end of an example of a half pipe cannula according to some embodiments disclosed herein.
Figure 7D:
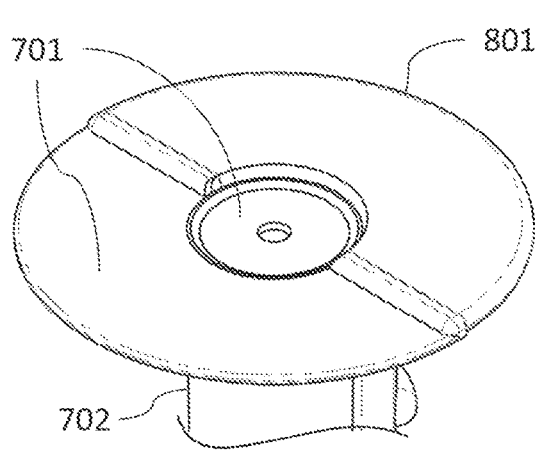
FIG. 7d depicts the proximal end of an example of a half pipe cannula according to some embodiments disclosed herein.

FIGS. 7b and 7c show embodiments of half pipe cannula 600 where rigid flange 801 wraps 360 degrees around flexible proximal tip 701, but the body of rigid portion 800 wraps less than 360 degrees around flexible elongated body 702. FIG. 7d shows an embodiment of half pipe cannula 600 with rigid flange 801 wrapping partially around flexible proximal tip 701 of half pipe cannula 600 and attaching to a flexible flange at proximal tip 701. The partial rigid flange and the partial flexible flange together wrap around the proximal end of half pipe cannula 600.

In addition to the various angle of wrapping rigid flange 801 around the proximal end of half pipe cannula 600, the height of rigid flange 801 may vary from implementation to implementation. For example, the overall height of rigid flange 801 shown in FIGS. 7a and 7b is taller than the overall height of rigid flange 801 shown in FIGS. 7c and 7d.

It may be advantageous for the flexible portion of the proximal end of half pipe cannula 600 to contain a variety of features. For example, in embodiments of half pipe cannula 600 shown in FIGS. 7b-7d, flexible proximal tip 701 is configured with a membrane which may prevent fluid from squirting the surgeon.

During instrument insertion and removal, fluid may squirt from the primary dam of a half pipe cannula into the cannula passage. The membrane disposed at flexible proximal tip 701 could prevent this squirting fluid from exiting the proximal end of half pipe cannula 600. This membrane could have many variations including, but are not limited to, different thicknesses, duck bill shapes, knife slits, hole sizes, and so on.

In some embodiments, the membrane may not be necessary, as exemplified in half pipe cannula 600 shown in FIG. 7a. In addition to, or in lieu of the membrane, a flexible flange could be added to the proximal end of half pipe cannula 600, as illustrated in FIG. 7d. Such a flexible flange may have the advantage of protecting the incision site, preventing elongated body 702 from collapsing, or prevent half pipe cannula 600 from slipping through the soft tissue portal.

As alluded to above, in some embodiments, half pipe cannula 600 can have a variety of distal tip features. FIGS. 8a1-8e depict non-limiting examples of half pipe cannula 600 with varying distal tips.

FIGS. 8a1, 8a2, 8d1, 8d2, and 8e depict embodiments of half pipe cannula 600 in which a flexible distal tip 703 does not significantly extend beyond a rigid distal tip 805. Leveraging the structural property (e.g., yield strength) of rigid distal tip 805, this arrangement may be advantageous to increase the ease of insertion of the half pipe cannula through a soft tissue portal.

Embodiments of half pipe cannula 600 shown in FIGS. 8b1, 8b2, 8c1, and 8c2 depict a flexible distal tip 703 which extends significantly beyond a rigid distal tip 805. This arrangement may be advantageous during instrument use by allowing the jaws of an instrument to articulate while the instrument is located within the passage of flexible portion 700.

FIGS. 8c1, 8c2, 8d1, 8d2, and 8e depict various embodiments of half pipe cannula 600 where flexible distal tip 703 includes a flexible flange. This flange may act to prevent half pipe cannula 600 from pulling out of the portal while removing an instrument from the half pipe cannula 600. Additionally, the flexible distal flange may retract some soft tissue in the surgical space which would improve visualization of the surgical site.

Those skilled in the art appreciate that the flange depicted in these embodiments of half pipe cannula 600 may have a number of variations which include, but are not limited to, various thicknesses, diameters, and shapes. Some examples of shapes may resemble large circles, small circles, ovals, flower pedals, or an asymmetric shape.

Additionally, the flange may include slits or gaps to allow for the flange to fold up during insertion of the cannula into the surgical site. These variations may aid in insertion of half pipe cannula 600 through the soft tissue portal and help during the use of the cannula after its insertion through the soft tissue portal.

Figure 8E:
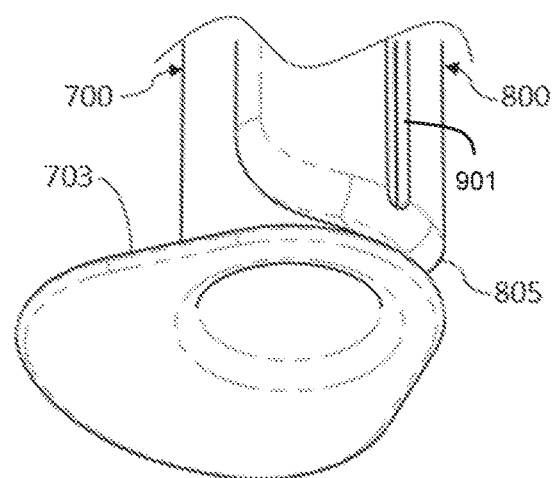
FIG. 8e depicts a perspective view of the distal end of an example of a half pipe cannula according to some embodiments disclosed herein.

Embodiments of half pipe cannula 600 shown in FIGS. 8c1, 8c2, 8d1, and 8d2 have distal flanges with circular shapes, while the embodiment of half pipe cannula 600 depicted in FIG. 8e shows a flange with a non-circular shape. In this latter embodiment of half pipe cannula 600, the distal flange has a small diameter located near the arc of the outer diameter of the cannula shared by rigid distal tip 805. This small diameter of the flange tapers towards a larger diameter feature on the opposite end of the flange, furthest away from the arc of the outer diameter of the cannula shared by rigid distal tip 805. A similar asymmetric and tapered shape may increase the ease in which half pipe cannula 600 with a flexible distal flange may insert through the soft tissue portal.

Figure 9A:
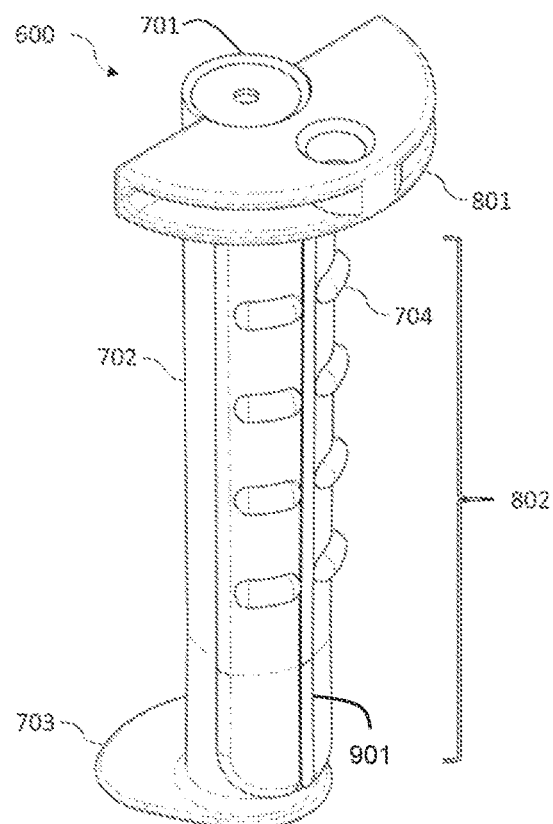
FIG. 9a depicts a perspective view of an example of a half pipe cannula according to some embodiments disclosed herein.
Figure 9B:
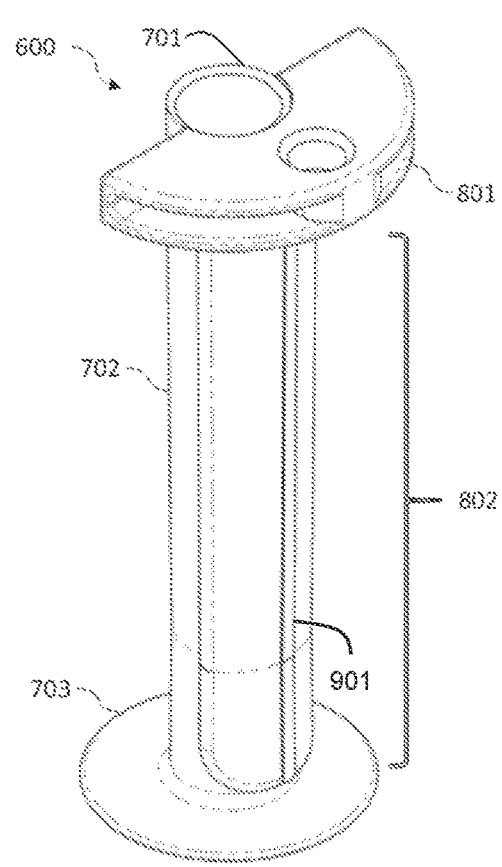
FIG. 9b depicts a perspective view of another example of a half pipe cannula according to some embodiments disclosed herein.

FIGS. 9*a* and 9*b* show further example embodiments of half pipe cannula 600 with and without surface features (e.g., threads, stubs, knobs, ridges, etc.) 704 on elongated tab 802. More specifically, FIG. 9*a* shows flexible surface features 704 which are part of flexible portion 700. These surface features are located on the exterior surface of elongated tab 802. Such surface features may aid in preventing the half pipe cannula from pushing into and pulling out of the soft tissue during instrument insertion and removal. In some cases, surface features 704 may be used to position half pipe cannula 600 after it is inserted through a soft tissue portal so that distal tip 703 is located at the inferior surface of the soft tissue while proximal flange 801 is located some distance above the patient's skin. Surface features 704 may allow for the position of half pipe cannula 600 to be adjusted throughout the surgery as the soft tissue swells and changes thickness so that the distal tip 703 is always located at the inferior surface of the soft tissue.

Depending upon application, surface features 704 can have a variety of thicknesses, profiles, lengths extending longitudinally and/or horizontally along elongated tab 802, and/or wrap around half pipe cannula 600. In some varieties of surface features 704, the pitch of surface features 704 may be constant or variable and may be located only near the distal tip or the proximal tip of half pipe cannula 600. In some embodiments, the pitch of surface features 704 may also be flat and depict ribbing, as shown in FIG. 9*a*. In one embodiment, surface features 704 may extend entirely around half pipe cannula 600. In another embodiment, surface features 704 may have a helical path around half pipe cannula 600. In still another embodiment, surface features 704 may be rigid and part of rigid portion 800 of half pipe cannula 600. Those skilled in the art appreciate that the example shown in FIG. 9*a* is non-limiting and that other configurations and/or arrangement of surface features 704 are possible. Further, surface features 704 may not be necessary in some embodiments of half pipe cannula 600. FIG. 9*b* shows one such example in which half pipe cannula 600 has no surface features, other than ridge 901 that extends along a longitudinal axis of elongated tab 802. Ridge 901 may be part of rigid portion 800 and may provide additional structural support for half pipe cannula 600. In some embodiments, half pipe cannula 600 may not have ridge 901 on elongated tab 802.

Figure 10A:
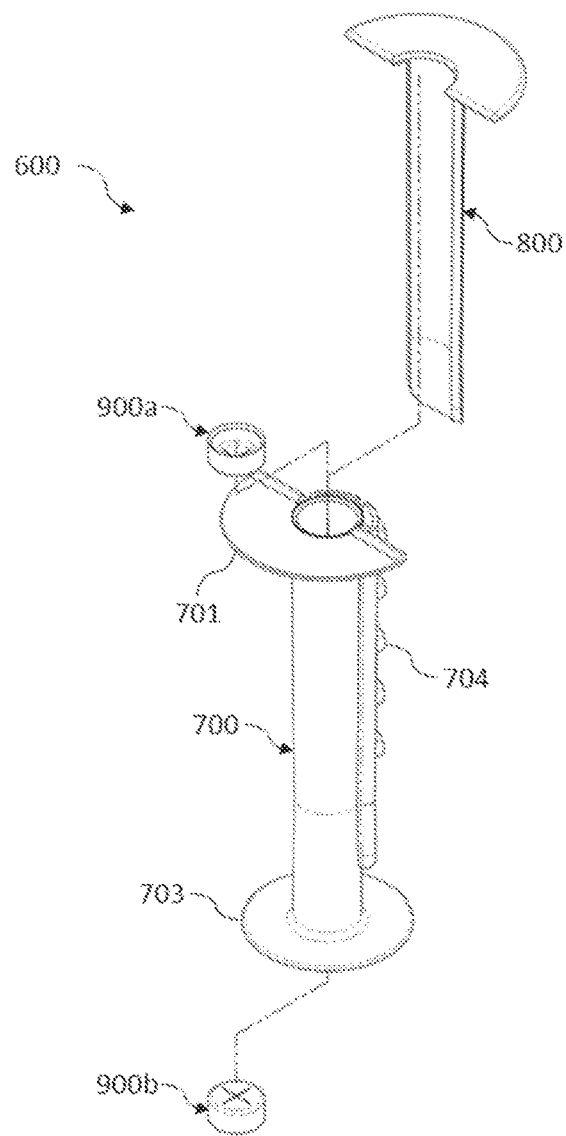
FIG. 10a depicts an exploded view of another example of a half pipe cannula according to some embodiments disclosed herein.

FIG. 10*a* shows an exploded view of another example of half pipe cannula 600 with various components. In this example, half pipe cannula 600 is composed of a rigid portion 800, a flexible portion 700, a secondary dam 900*a*, and a secondary dam 900*b*.

Figure 10B:
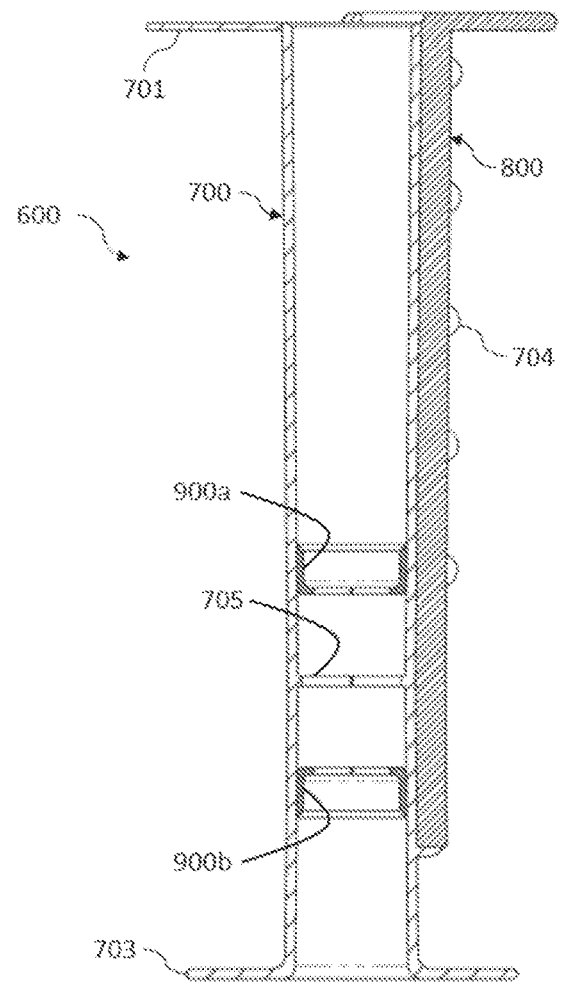

As shown in FIG. 10*b*, which depicts a cross-sectional view of half pipe cannula 600 of FIG. 10*a*, secondary dams 900*a* and 900*b* may be positioned between primary dam 705 and proximal end 701 of flexible portion 700 or between primary dam 705 and distal end 703 of flexible portion 700. It may also be advantageous for these dams to be located near to or at the proximal or distal ends of half pipe cannula 600. Additionally, it may be advantageous for these dams to be located at a position approximately halfway between the distal end and proximal end of half pipe cannula 600.

The addition of secondary dams 900*a* and 900*b* to primary dam 705 provides half pipe cannula 600 with an improved ability to resist leaking of fluid through its passage. It may be advantageous for the primary and secondary dams to be located along the length of half pipe cannula 600 in such a way that a gap exists between each secondary dam 900*a* and 900*b* and primary dam 705. It may also be advantageous to have any number of secondary dams 900*a* and 900*b* present in half pipe cannula 600 including, but are not limited to, 1 to 10 of these secondary dams. It is appreciated that secondary dams 900*a* and 900*b* and primary dam 705 may contain openings for the purpose of preventing fluid from passing through the dam while also allowing instruments to pass through the dam(s). These openings flex around an instrument when an instrument is passed through the dams and close when the dams are in their stable state.

These openings in combination with the shape of primary dam 705 and secondary dams 900*a* and 900*b* may take the form of any number of shapes, lengths, thicknesses, orientations, and combination thereof, including but not limited to, circular hole(s), ovular opening(s), knife slit(s), tri-slits, duck bill(s), straight slit, quad-slits, overlapping flaps, small aperture(s), etc. These slits may preferably be long enough to allow instruments to pass though the dams without damaging the dams, even when the instrument has a diameter only slightly smaller than the inner diameter of flexible portion 700 of half pipe cannula 600.

Although FIGS. 10*a* and 10*b* show dams with a flat surface in which the slit is present, it would also be evident to one skilled in the art that primary dam 705 and secondary dams 900*a* and 900*b* could be any shape including but not limited to round or conically shaped. The thickness of primary dam 705 and secondary dams 900*a* and 900*b* should be thick enough to prevent fluid from flowing through the dam while preventing significant resistance to passing instruments through the dams. It is evident to those skilled in the art that secondary dams 900*a* and 900*b* could be included in any embodiment of half pipe cannula 600 disclosed herein with a variety of proximal ends, elongated bodies, and distal ends. It is also evident that, in some embodiments of half pipe cannula 600, only primary dam 705 would be present.

FIGS. 11*a*, 11*b*, 12*a*, and 12*b* depict another type of half pipe cannulas. This type of half pipe cannulas combines an off-the-shelf fully flexible cannula 200 with a rigid portion 800. Since fully flexible cannula 200 may be readily available on the market, rigid portion 800 can be manufactured independently of fully flexible cannula 200 and then assembled with fully flexible cannula 200 to form half pipe cannula 600.

As discussed above, fully flexible cannula 200 may mainly consist of a fully flexible elongated body with a cannulated passage extending between a proximal end and a distal end thereof, a dam disposed in the cannulated passage, a flange at the proximal end and/or a flange at the distal end. To provide rigidity to half pipe cannula 600, rigid portion 800 may be affixed or otherwise attached to the elongated body of fully flexible cannula 200 using a variety of ways including, but are not limited to, sonic welding, overmolding, adhering, taping, or through the use of other mechanical or chemical fixation techniques. Rigid portion 800 may be affixed partially or fully to fully flexible cannula 200. Further, rigid portion 800 may be affixed along its length and/or on its proximal flange.

Figures 11A, 11B:
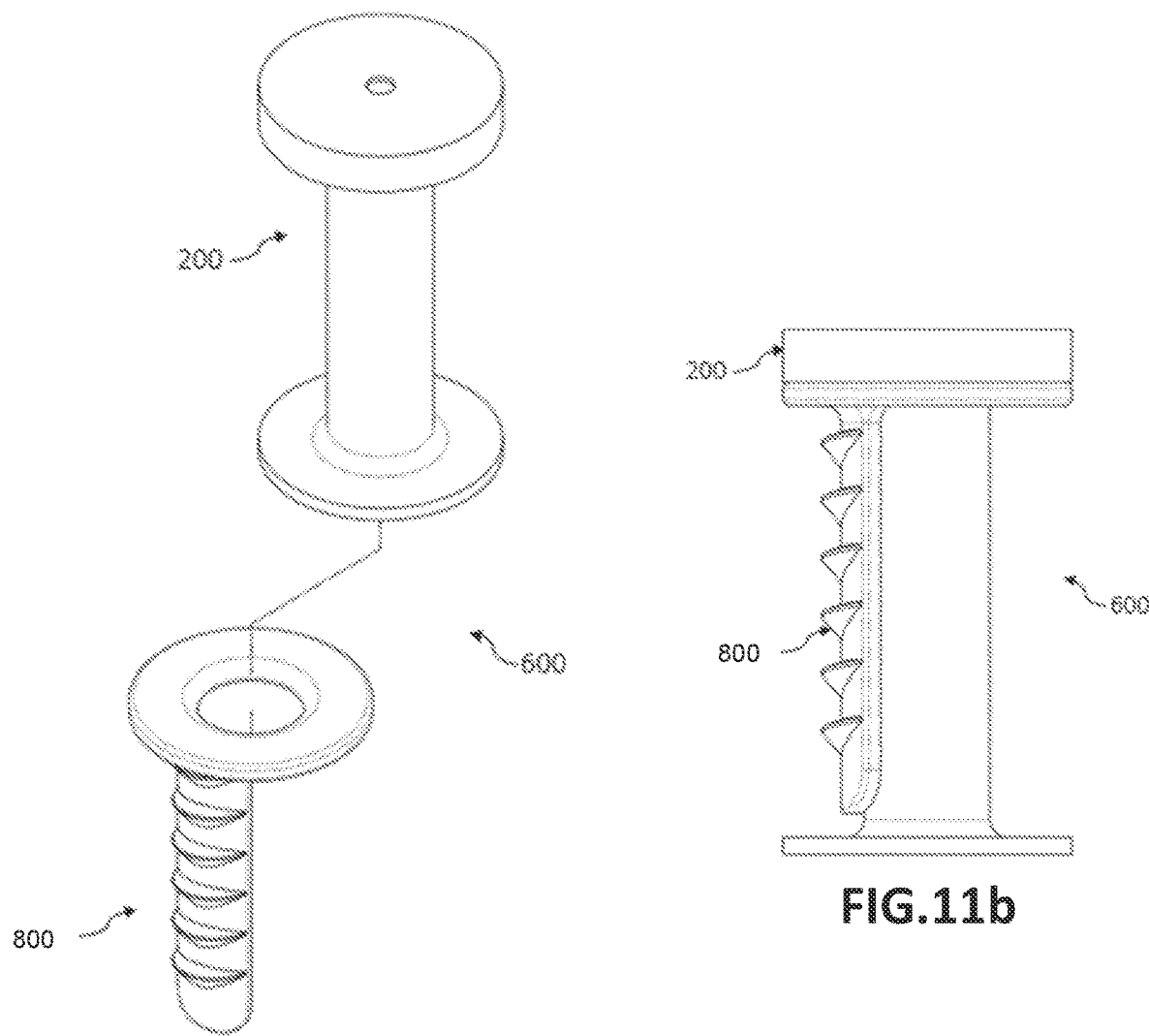

In the example of FIGS. 11*a* and 11*b*, rigid portion 800 may contain surface features (e.g., threads) which could be rigid, flexible, or a combination of rigid and flexible. Similar to surface features 704 described above, these surface features can be the same size and pitch or may have variable size and pitch. As exemplified in FIGS. 11*a*-11*b*, rigid portion 800 may have a rigid flange at its proximal end. This rigid flange may be of a variety of thicknesses and may wrap around the entire or at least a portion of the proximal end of fully flexible cannula 200.

In the example shown in FIGS. 11*a*-11*b*, rigid portion 800 is located beneath the proximal flange of fully flexible cannula 200. It may be advantageous for the proximal flange of rigid portion 800 to touch the bottom surface of the proximal flange of fully flexible cannula 200 or be located any distance below or above it. Additionally, the distal tip of rigid portion 800 may extend to very close to the proximal surface of the distal flange located on fully flexible cannula 200. It is appreciated that this distal tip of rigid portion 800 may be located at any length along fully flexible cannula 200.

Figure 12A:
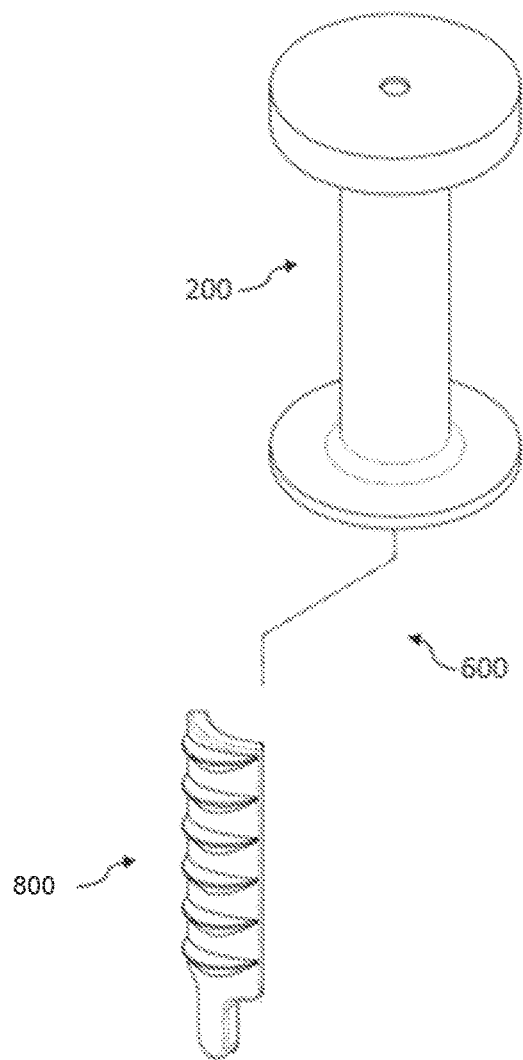
FIG. 12a depicts an exploded view of another example of a half pipe cannula according to some embodiments disclosed herein.
Figure 12B:
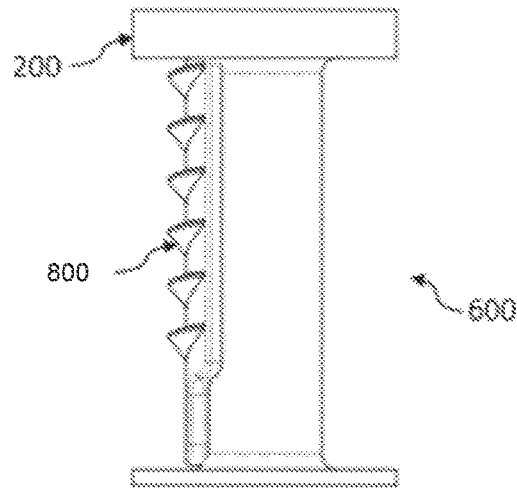

FIGS. 12*a* and 12*b* depict another example of half pipe cannula 600 with features similar to those described above with reference to FIGS. 11*a* and 11*b*. However, in this example, rigid portion 800 does not contain a flange on its proximal end. Further, the proximal end of rigid portion 800 is located close to the proximal flange of fully flexible cannula 200. It is appreciated that this proximal tip of rigid portion 800 could be touching the distal surface of the proximal flange of fully flexible cannula 200. In some embodiments, the proximal end of rigid portion 800 could be located any distance below the proximal flange of fully flexible cannula 200.

In some embodiments, the distal tip of rigid portion 800 is located almost touching the proximal surface of the distal flange of fully flexible cannula 200. It is appreciated that the distal tip of rigid portion 800 could be located any distance proximal to the distal flange of fully flexible cannula 200. As illustrated in FIG. 12*a*, the distal tip of rigid portion 800 can be of a unique shape that is generally narrower than the width of rigid portion 800. The actual shape and size of the distal tip of rigid portion 800 can vary from implementation to implementation to aid in the insertion of half pipe cannula 600 through a soft tissue portal.

As a non-limiting example, the distal tip of rigid portion 800 can have a long thin feature extending approximately the same distance as the distance between the outer diameter of the distal flange of fully flexible cannula 200 is from the outer diameter of the elongated body of fully flexible cannula 200. The distal tip of rigid portion 800 must have sufficient structural integrity (e.g., yield strength) to not break or deform significantly while being inserted into a portal. Further, the distal tip of rigid portion 800 must be shaped in such a way that allows for the flange to fold up and pass through the incision. The distal tip of rigid portion 800 could be shaped in a variety of ways, including but not limited to, spoon shaped, pointed, flat, with rounded edges, etc. Furthermore, various surface features may be incorporated as discussed above.

Figure 13A:
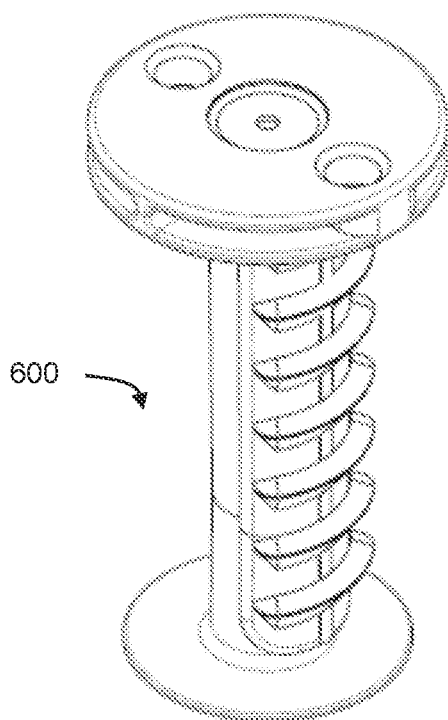
FIG. 13a depicts a perspective view of a preferred embodiment of a half pipe cannula.
Figure 13B:
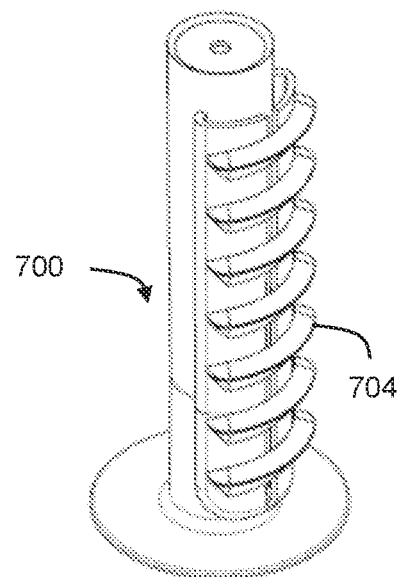
Figure 13C:
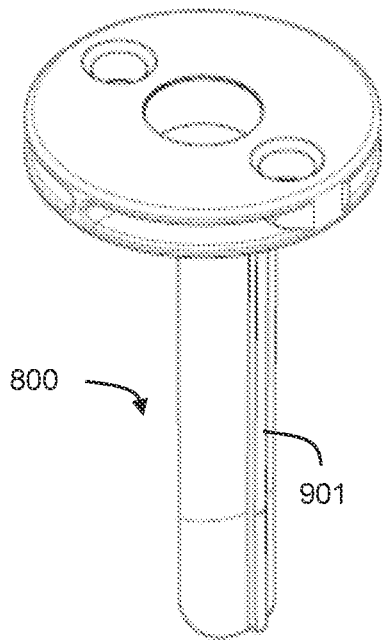

FIG. 13*a* depicts a perspective view of a preferred embodiment of half pipe cannula 600 having a flexible portion 700 as shown in FIG. 13*b* and a rigid portion 800 as shown in FIG. 13*c*. In this embodiment, rigid portion 800 includes an elongated tab with ridge 901 extending along the length thereof and flexible portion 700 wraps around rigid portion 800, with surface features 704 crossing over ridge 901 of rigid portion 800.

Figure 13D:
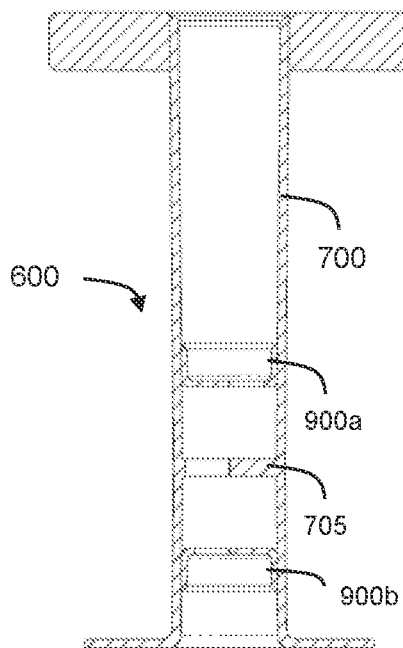
FIG. 13d depicts a cross-sectional view of the half pipe cannula of FIG. 13a with multiple dams.
Figure 13E:
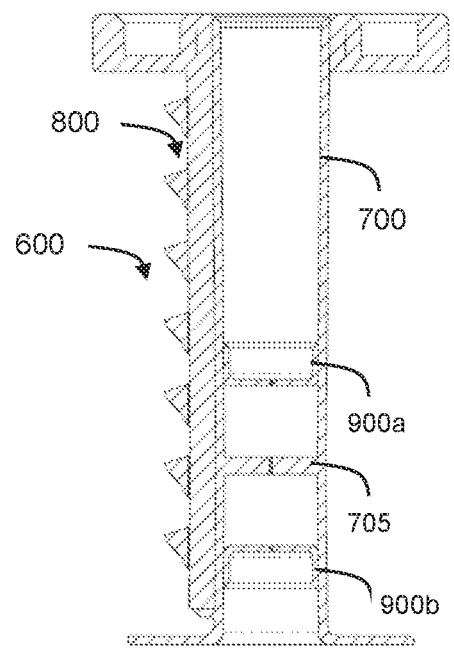
FIG. 13e depicts another cross-sectional view of the half pipe cannula of FIG. 13a with multiple dams.
Figure 13F:
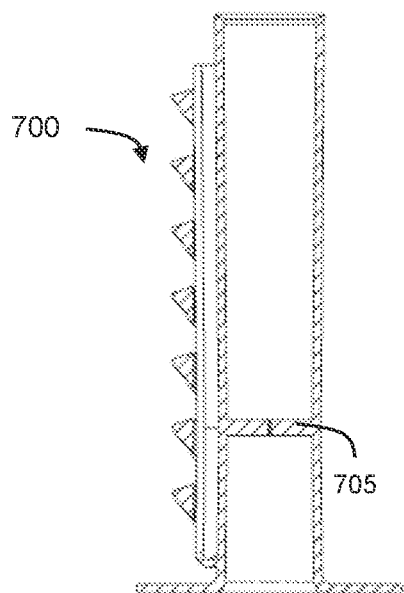
FIG. 13f depicts a cross-sectional view of the flexible portion of the half pipe cannula of FIG. 13a with a single dam.

As illustrated in FIGS. 13*d*-13*e*, which depict cross-sectional views of half pipe cannula 600 of FIG. 13*a*, flexible portion 700 can have a cannulated passage with multiple dams, with secondary dams 900*a* and 900*b* placed on both sides of primary dam 705. Alternatively, flexible portion 700 can have a single dam 705, as shown in FIG. 13*f*.

One key distinguishing feature of a half pipe cannula disclosed herein is that the rigid portion does not fully enclose the flexible portion. This is a unique feature of the half pipe cannula as compared with existing cannulas which are fully enclosed around the cannulas body and/or dam(s). For this reason, the half pipe cannula presents a new challenge to determine how much of the rigid portion should enclose the flexible portion.

From the surgical perspective, it can be appreciated that in general the rigid portion should be as small as possible to allow the cannula to remain flexible for use with instruments. Conversely, the cannula must be rigid enough along its length for the rigid portion to aid in helping to push and pull the flexible portion through the portal.

Additionally, this rigidity must allow the user to be able to reposition and pull back on the cannula after the cannula has already been positioned into the surgical space. Also, it is important that the strength of the rigid portion be strong enough to withstand all of the forces associated with arthroscopy. Forces are exerted on the cannula during instrument maneuvering, instrument articulation, cannula adjustment after insertion, and cannula removal. However, the cannula will likely see the greatest forces during cannula insertion through the portal.

Because of these conflicting interests, the rigidity of the cannula must be carefully chosen. Several factors may contribute to the strength of the rigid portion of the cannula. The cannula's strength is related to its resistance to deflection, cracking, shearing, and breaking.

Figure 14A:
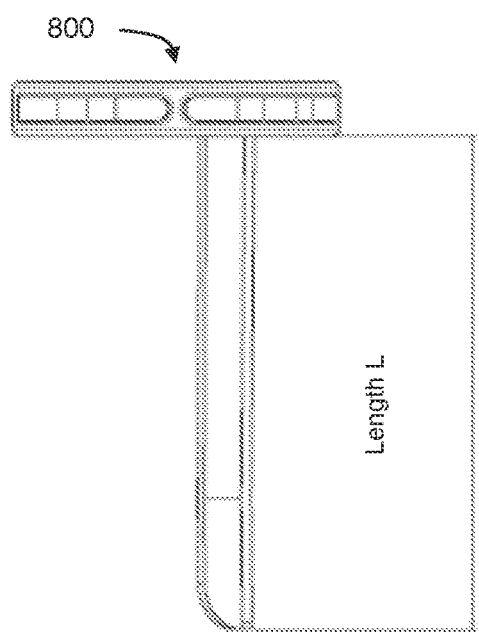
FIGS. 14a-14c depict dimensions of an example of a half pipe cannula according to a preferred embodiment disclosed herein.
Figure 14B:
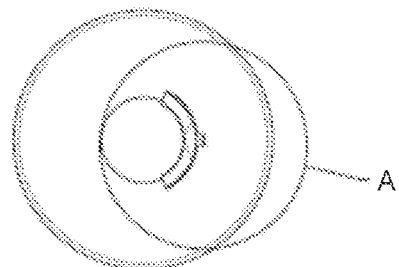
Figure 14C:
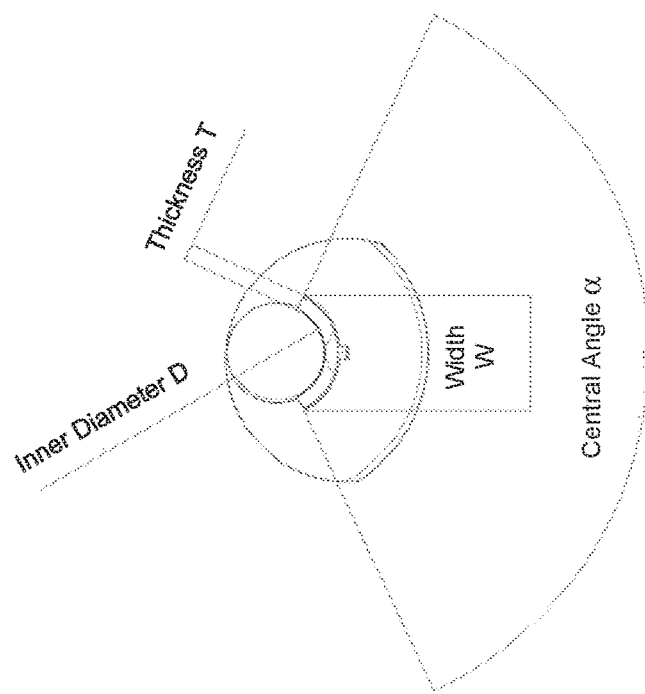

Referring to FIGS. 14*a*-14*c*, which depict dimensions of an example of a half pipe cannula according to a preferred embodiment disclosed herein, the primary factors affecting the strength of the rigid portion of a half pipe cannula disclosed herein are the Length (L), Thickness (T), Inner Diameter (D), Width (W), and Central Angle (Alpha). It is understood that the longer that Length is, the more likely that the rigid portion of a half pipe cannula is to break during introduction through a portal. However, the length of the cannula must still be long enough to access the surgical site.

Because of this balance, the half pipe cannula's Length L should range from 20 to 120 mm. A length of 40 mm may be usable with most patients.

The Thickness T is desired to be as small as possible, to limit resistance when the half pipe cannula is pushed through the portal during cannula insertion, but large enough to prevent the half pipe cannula from breaking. This dimension can have a range between 0.25 and 3 mm, while 1.5 mm is a likely value as it balances the two factors.

The Inner Diameter D must be large enough for instruments to be passed through the half pipe cannula during surgery. Additionally, the larger the Inner Diameter, the more strength it contains to resist insertion forces. However, the Inner Diameter cannot be too large as it would create resistance to the cannula being inserted through the portal. Because of this balance, the Inner Diameter may range from 4 mm to 12 mm, but a preferred value would be 8 mm. This dimension is acceptable in the industry as it facilitates most surgical instruments used in arthroscopy.

The Width W and the Central Angle Alpha are related to one another. These two dimensions indicate how much of the rigid portion will ultimately wrap around or cover the flexible portion of the half pipe cannula. The greater the Central Angle is the greater the Width W becomes and the smaller the Central Angle is the smaller the Width becomes. The larger the Central Angle is, the more resistance the surgeon will feel while moving instruments during instrument passing, instrument positioning, and instrument articulation. Additionally, the larger the Central Angle, the more resistance the surgeon will feel while introducing the cannula through the portal. It is also appreciated that the larger the Central Angle, the more strength the half pipe cannula will have to resist forces seen during the cannula's introduction through the portal, removal from the portal, and use during surgery. This Central Angle must be balanced to allow for the cannula to be strong enough to resist forces seen during surgery and small enough to allow the surgeon flexibility while using instruments with the half pipe cannula. This Central Angle may range from 30 to 270 degrees and the Width may range from 4 mm to 15 mm. In some embodiments, a Central Angle of 130 degrees and a Width of 11 mm may be preferred.

In the case that a cross-sectional profile of a half pipe cannula (e.g., FIG. 14c) contains a shape other than a circle along its central axis, some of these factors will be more or less meaningful. In particular, the Inner Diameter and Central Angle may be less important and the Width, Thickness, and Length may be more important.

The detailed description and the specific examples described above, while indicating the preferred embodiments, are given by way of illustration only and not by way of limitation. Descriptions of known materials and manufacturing techniques may be omitted so as not to unnecessarily obscure the disclosure in detail. Various substitutions, modifications, additions and/or rearrangements within the spirit and/or scope of the underlying inventive concept will become apparent to those skilled in the art from this disclosure.

As used herein, the terms "comprises," "comprising," "includes," "including," "has," "having," or any other variation thereof, are intended to cover a non-exclusive inclusion. For example, a process, product, article, or apparatus that comprises a list of elements is not necessarily limited only those elements but may include other elements not expressly listed or inherent to such process, product, article, or apparatus.

Furthermore, the term "or" as used herein is generally intended to mean "and/or" unless otherwise indicated. For example, a condition A or B is satisfied by any one of the following: A is true (or present) and B is false (or not present), A is false (or not present) and B is true (or present), and both A and B are true (or present). As used herein, a term preceded by "a" or "an" (and "the" when antecedent basis is "a" or "an") includes both singular and plural of such term, unless clearly indicated otherwise (i.e., that the reference "a" or "an" clearly indicates only the singular or only the plural). Also, as used in the description herein, the meaning of "in" includes "in" and "on" unless the context clearly dictates otherwise.

It will also be appreciated that one or more of the elements depicted in the drawings/figures can also be implemented in a more separated or integrated manner, or even removed or rendered as inoperable in certain cases, as is useful in accordance with a particular application, use case, or implementation. Additionally, any signal arrows in the drawings/figures should be considered only as exemplary, and not limiting, unless otherwise specifically noted.

It should be understood that the inventive concepts disclosed herein are capable of many other modifications. To the extent such modifications fall within the scope of the appended claims and their equivalents, they are intended to be covered by this patent. It should also be understood that the term "a" as used herein generally means "one or more" and is not intended to be construed in a singular sense. In addition, the operations described in connection with the methods of the disclosure need not necessarily be executed in the sequence described, as they may be executed in a different sequence consistent with the principles of the disclosure. The scope of the invention should be determined by the following claims and their legal equivalents.

What is claimed is:

1. A half pipe cannula, comprising:
a flexible portion having a proximal end, a distal end, and an elongated body extending between the proximal end and the distal end, the elongated body of the flexible portion having a cannulated passage; and
a rigid portion having a proximal end, a distal end, and a non-cylindrical elongated body with a proximal end, a distal end, and a length between the proximal end and the distal end of the non-cylindrical elongated body of the rigid portion, the non-cylindrical elongated body of the rigid portion partially wrapping around the circumference of the flexible portion along the length between the proximal end and the distal end of the non-cylindrical elongated body of the rigid portion such that a surface area of the flexible portion is exposed circumferentially unhindered along a length corresponding to the length of the non-cylindrical elongated body of the rigid portion.

2. The half pipe cannula of claim 1, wherein the flexible portion has surface features.

3. The half pipe cannula of claim 2, wherein the surface features include a thread, a rib, a stud, a protrusion, a knob, or a combination thereof.

4. The half pipe cannula of claim 2, wherein the rigid portion has a ridge extending along a longitudinal axis of the non-cylindrical elongated body of the rigid portion.

5. The half pipe cannula of claim 2, wherein the surface features extend over the rigid portion at least partially.

6. The half pipe cannula of claim 1, wherein the rigid portion has a rigid flange on the proximal end of the rigid portion.

7. The half pipe cannula of claim 6, wherein the rigid flange on the proximal end of the rigid portion has one or more engagement features for engaging with an instrument.

8. The half pipe cannula of claim 6, wherein the flexible portion has a flexible flange at least partially attached to the rigid flange, at the proximal end of the flexible portion.

9. The half pipe cannula of claim 6, wherein the rigid portion is made of a plurality of components.

10. The half pipe cannula of claim 1, wherein the rigid portion has surface features, wherein the surface features include a thread, a rib, a stud, a protrusion, a knob, or a combination thereof.

11. The half pipe cannula of claim 1, wherein the flexible portion has a flexible flange on the distal end of the flexible portion.

12. The half pipe cannula of claim 1, wherein the flexible portion includes one or more dams disposed within the cannulated passage.

13. The half pipe cannula of claim 12, wherein the one or more dams are disposed within the cannulated passage toward the distal end or the proximal end of the flexible portion.

14. The half pipe cannula of claim 1, wherein the flexible portion is made of a plurality of components.

15. The half pipe cannula of claim 1, wherein the non-cylindrical elongated body of the rigid portion comprises a plurality of components.

16. The half pipe cannula of claim 1, wherein the distal end of the flexible portion extends beyond the distal end of the rigid portion.

17. The half pipe cannula of claim 1, wherein the distal end of the rigid portion is proximate or touches the distal end of the flexible portion.

18. The half pipe cannula of claim 1, wherein the rigid portion has a length ranging from 20 mm to 120 mm and a thickness ranging from 0.25 mm to 3 mm.

19. The half pipe cannula of claim 1, wherein the cannulated passage has an inner diameter ranging from 4 mm to 12 mm.

20. The half pipe cannula of claim 1, wherein the flexible portion has an asymmetric cross-sectional profile.

21. The half pipe cannula of claim 1, wherein the flexible portion consists of a flexible cannula with a first flange at the proximal end and a second flange at the distal end.

\* \* \* \* \*